(12) United States Patent
Park et al.

(10) Patent No.: US 10,631,978 B2
(45) Date of Patent: Apr. 28, 2020

(54) PROSTHETIC HEART VALVE

(71) Applicant: Strait Access Technologies Holdings (Pty) Ltd, Cape Town (ZA)

(72) Inventors: Kenneth Stuart Park, Cape Town (ZA); Harish Appa, Cape Town (ZA); Claude Visagie, Cape Town (ZA); Deon Bezuidenhout, Cape Town (ZA); Peter Paul Zilla, Cape Town (ZA)

(73) Assignee: Strait Access Technologies Holdings (Pty) Ltd, Cape Town (ZA)

( * ) Notice: Subject to any disclaimer, the term of this patent is extended or adjusted under 35 U.S.C. 154(b) by 0 days.

(21) Appl. No.: 14/784,568

(22) PCT Filed: Apr. 17, 2014

(86) PCT No.: PCT/IB2014/060816
§ 371 (c)(1),
(2) Date: Oct. 14, 2015

(87) PCT Pub. No.: WO2014/170870
PCT Pub. Date: Oct. 23, 2014

(65) Prior Publication Data
US 2016/0067038 A1 Mar. 10, 2016

(30) Foreign Application Priority Data

Apr. 19, 2013 (GB) .................................. 1307143.6
Apr. 19, 2013 (GB) .................................. 1307144.4

(51) Int. Cl.
*A61F 2/24* (2006.01)
(52) U.S. Cl.
CPC .............. *A61F 2/2418* (2013.01); *A61F 2/24* (2013.01); *A61F 2/2406* (2013.01); *A61F 2/2412* (2013.01); *A61F 2/2415* (2013.01)

(58) Field of Classification Search
CPC ......... A61F 2/2418; A61F 2/2412; A61F 2/24
See application file for complete search history.

(56) References Cited

U.S. PATENT DOCUMENTS 5,800,527 A 9/1998 Jansen et al.
6,174,331 B1 1/2001 Moe et al.
(Continued)

FOREIGN PATENT DOCUMENTS

CN 1244107 A 2/2000
WO WO2007130537 A1 11/2007
(Continued)

OTHER PUBLICATIONS

Mohammadi et al.; Design and simulation of a poly(vinyl alcohol)-bacterial cellulose nanocomposite mechanical aortic heart valve prosthesis; Journal of Engineering in Medicine; vol. 23 Part H (2009); pp. 697-711.*
(Continued)

*Primary Examiner* — Dinah Baria
(74) *Attorney, Agent, or Firm* — Rudy J. Ng; Bret E. Field; Bozicevic, Field & Francis LLP

(57) ABSTRACT

A prosthetic heart valve (10) which includes a stent (14) having three leaflets (12) attached thereto is provided. The stent (14) is compressible so as to be capable of being introduced into a patient's body through a minimally invasive procedure and has a ring-like body (16) defining in its height three arch-shaped elements (18). Each element (18) includes an arc (20) and a pair of haunches (22) extending from opposite sides thereof, with three commissural posts (26) formed by the haunches (22) of adjacent elements (18). The leaflets (12) each have an attachment edge (28) and a free edge (30) with a belly (32) extending therebetween. The leaflets (12) are movable between a coapted condition, in which the free edges (30) abut and prevent fluid flow through the valve (10), and an open condition, in which fluid
(Continued)

flow through the valve (10) is permitted. The leaflets (12) are made from a polymeric material and are moulded directly onto the stent (14) so as to provide for continuous attachment thereof.

14 Claims, 16 Drawing Sheets

(56) References Cited

U.S. PATENT DOCUMENTS

| | | | |
|---|---|---|---|
| 6,562,069 B2* | 5/2003 | Cai | A61F 2/2412 623/2.12 |
| 2004/0186563 A1 | 9/2004 | Lobbi | |
| 2006/0122692 A1 | 6/2006 | Gilad et al. | |
| 2006/0122693 A1 | 6/2006 | Biadillah et al. | |
| 2006/0136037 A1* | 6/2006 | DeBeer | A61F 2/91 623/1.15 |
| 2009/0157175 A1 | 6/2009 | Benichou | |
| 2011/0137397 A1* | 6/2011 | Chau | A61F 2/2418 623/1.11 |
| 2012/0078357 A1 | 3/2012 | Conklin | |
| 2014/0005772 A1* | 1/2014 | Edelman | A61F 2/2412 623/2.17 |

FOREIGN PATENT DOCUMENTS

| | | | |
|---|---|---|---|
| WO | WO2009042196 A3 | 4/2009 | |
| WO | WO 2012/032187 A1 * | 3/2012 | |

OTHER PUBLICATIONS

International Search Report and Written Opinion for PCT/IB2014/060816 dated Nov. 11, 2014, 10 pages.

First Examination Report for Indian Patent Application No. 3534/KOLNP/2015, dated Jan. 9, 2020, 7 pages.

* cited by examiner

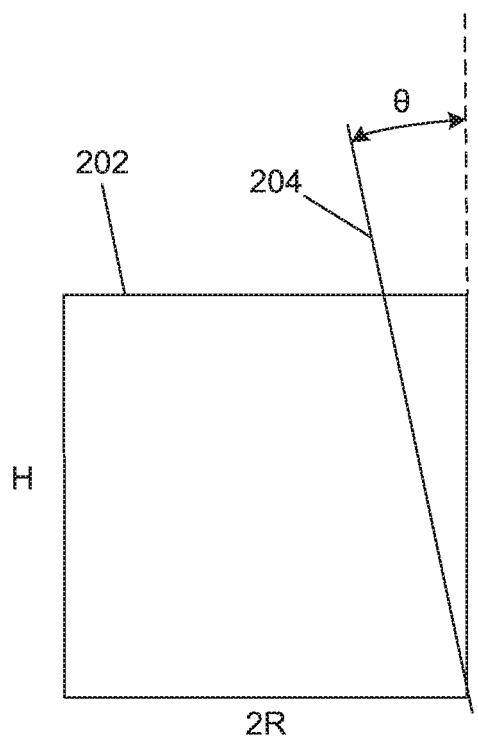
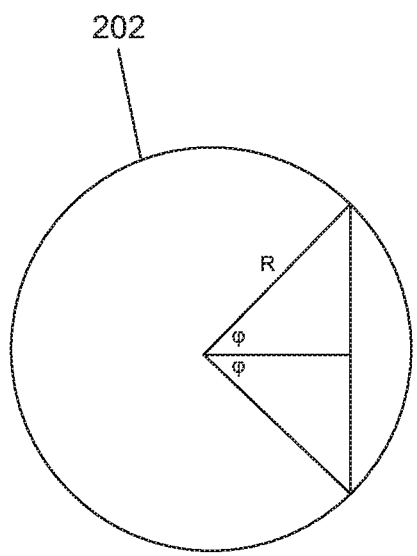
Figure 12
Figure 13
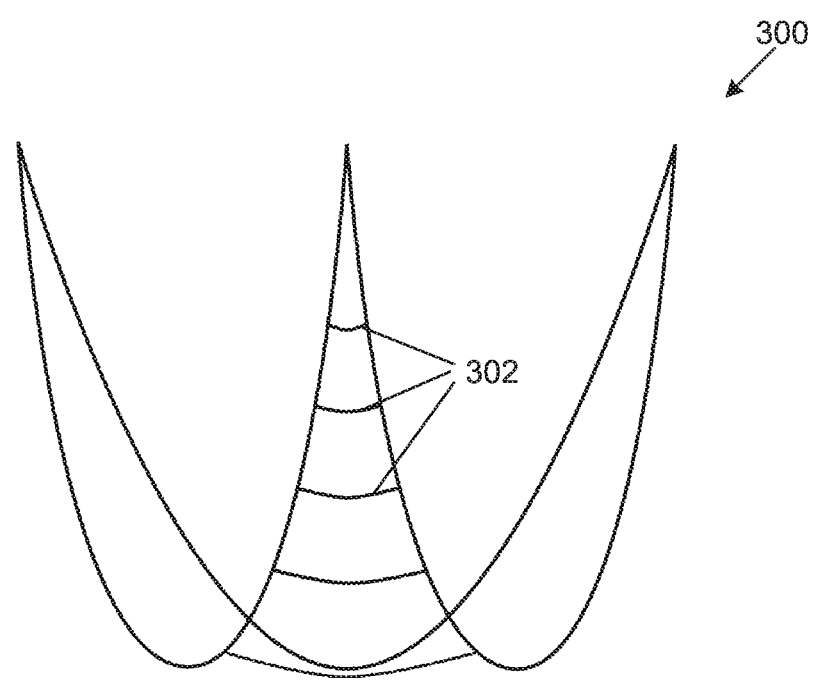
Figure 14

PROSTHETIC HEART VALVE

FIELD OF THE INVENTION

This invention relates to prosthetic heart valves, including stents and leaflets for prosthetic heart valves that are placed using minimally invasive procedures.

BACKGROUND TO THE INVENTION

Heart failure is one of the highest causes of death worldwide. A common form of heart failure occurs due to the malfunctioning of diseased heart valves, and it is estimated that between 275,000 and 370,000 valve replacement procedures are performed each year. During such procedures, a prosthetic valve is implanted into an annular opening in the heart of a patient, typically after surgical removal of a diseased, damaged or malfunctioning natural valve.

Traditional heart valve replacement methods, which are still widely used today, require that a patient undergo open heart surgery. Open heart surgery involves the physical separation of a patient's breastbone so as to allow access to the heart. This replacement method not only leaves considerable scars, but may also pose a risk to infection, bleeding as well as requiring long hospitalisation and recovery periods.

In order to overcome the disadvantages and risks of open heart surgery, a number of minimally invasive techniques or procedures have been developed. The most common forms of minimally invasive procedures used for heart valve replacement are known as endovascular procedures, where the incision or access point is through a blood vessel, such as the femoral artery. The procedure is carried out percutaneously and transluminally using the vascular system to convey appropriate devices to the desired position in the body. Minimally invasive surgical techniques include transapical techniques, whereby a mini-thoracotomy is performed and the replacement heart valve is inserted directly through the apex of the heart.

The use of endovascular procedures during heart valve replacement has led to the development of replacement valves capable of being reduced in size, also referred to as crimping, so as to be capable of being moved through a blood vessel and then later to be expanded to a desired size once deployed. Expandable heart valves currently used typically make use of self-expandable materials for the valve stent and are compressed into a valve deployment device. Balloon-expandable valves, for which materials such as stainless steel or nickel-cobalt-chromium alloys are used for the stent, are also commonly used.

Leaflets, typically made from stabilized tissue of animal origin, such as bovine or porcine pericardium, are attached to the stent typically by means of stitching the leaflets onto the stent frame, normally along a pericardium or fabric skirt, or by means of direct stitching to the stent frame in the case of xenograft valves. Polymeric leaflets have also been proposed which may be attached to the stent by means of stitching, gluing or other means.

In the case of tri-leaflet valves, the leaflets are generally attached to three shaped posts of the stem along an attachment edge and adjacent leaflets typically join at such posts to provide a commissure. The leaflet edge extending between the two commissures is generally referred to as the free edge, while the generally curved leaflet area between the free edge and the attachment edge is known as the belly.

Various leaflet designs, particularly polymeric leaflets, have been developed in recent years, however, these have a number of potential drawbacks. Designs causing overly close coaptation of the leaflets may limit wash-out of blood during haemodynamic function, particularly in the regions close to the stent posts at the commissures. These regions, also referred to as regions of stagnation, may encourage local thrombogenesis, and may lead to further restriction of the valve orifice in the longer term.

Another disadvantage of certain existing designs is that the valve leaflets may not fully close in the coaptive region. This may result in excessive regurgitation upon closure of the artificial valve. Furthermore, valve leaflet design may cause high stresses at commissures or in regions of the leaflet belly, which may lead to leaflet damage or valve malfunction.

Some leaflet designs may lead to insufficient orifice size when the artificial valve leaflets are in an open position. This may result in a high pressure drop across the valve, which can in turn limit haemodynamic performance of the artificial valve.

In addition to the potential leaflet design drawbacks set out above, a major drawback experienced with minimally invasive procedures and thus prosthetic heart valves that may be introduced by such procedures, is that the procedures require highly specialised equipment which has the effect that such procedures are highly expensive. The cost of replacing a defective heart valve typically ranges from about US$60,000 to US$100,000, thus making such procedures generally only available to the developed world.

The term "polymer" in this specification shall have its widest meaning and includes plastics materials suitable for use in the human body, such as polyurethanes, and also includes reinforced polymers, such as fibre reinforced polymers, and composites constructed using polymers.

SUMMARY OF THE INVENTION

In accordance with the invention there is provided a prosthetic heart valve which includes a stent having three leaflets attached thereto, the stent being compressible to a compressed condition in which it is capable of being introduced into a patient's body through a minimally invasive procedure and further being expandable from the compressed condition to an operative condition during deployment of the valve within the patient's body, the stent having a ring-like body with an inlet and an outlet and defining in its height three arch-shaped elements each of which has an arc and a pair of haunches extending from opposite sides thereof, with three commissural posts formed by the haunches of adjacent elements, each leaflet having an attachment edge and a free edge with a belly extending between the free edge and the attachment edge, the leaflets being movable between an open condition, in which fluid flow through the valve is permitted in a direction from the inlet to the outlet, and a coapted condition, in which the free edges abut and prevent fluid flow through the valve in an opposite direction from the outlet to the inlet, characterized in that the leaflets are made from a polymeric material and are moulded directly onto the stent so that the attachment edge of each leaflet is continuously attached along the length of an arch-shaped element.

Further features of the invention provide for the arch-shape to be defined by a parametric curve and its mirror image along the z-axis which is wrapped about a cylinder having a diameter of the prosthetic heart valve; for the parametric curve to be defined by a function $A(x)=(1-x)^3 P_0+3(1-x)^2 x P_1+3(1-x)x^2 P_2+x^3 P_3$, with $P_0$ to $P_3$ being control points; for $P_0$ and $P_3$ to be selected on the basis of the diameter and height of prosthetic heart valve; and for $P_1$ to be selected from the range of $0 \leq z \leq H$ and $P_2$ to be selected from the range $0 \leq x \leq \pi D/6$ with H being the height and D the diameter of the prosthetic heart valve.

Still further features of the invention provide for the free edge of the leaflets to be defined by three curves defined by functions y=mx with $-c_b \leq x < -c_b+x_s$, y=K cos(Lx)+t with $-c_b+x_s \leq x < c_b-x_s$, and y=-mx with $c_b-x_s \leq x \leq c_b$ with the constant m being in the range of 0.1 to 1, the constant K being in the range of −3 to 0, the constant L being in the range of 0.05 to 1.5, and the constant t being in chosen such that the end points of the three curves meet each other.

Yet further features of the invention provide for the belly to be defined by a parametric curve in a two dimensional plane; for the parametric curve to be defined by a function $B(x)=(1-x)^3 P_0 + 3(1-x)^2 x P_1 + 3(1-x) x^2 P_2 + x^3 P_3$, with $P_0$ to $P_3$ being control points; for $P_2$ and $P_3$ to remain constant; and for $P_0$ to be selected from the range of $0.3D \leq P_{0x} \leq 0.5D$ and $0.5H \leq P_{0y} \leq 0.8H$ and $P_1$ to be selected from the range $0.4D \leq P_{1x} \leq 0.6D$ and $0.3H \leq P_{1y} \leq 0.8H$ with H being the height and D the diameter of the prosthetic heart valve.

Further features of the invention provide for stent to include reinforcing members that act to strengthen the stent so as to support the leaflets during movement between the coapted condition and the open condition and to secure the stent within a valve annulus; and for the reinforcing members to span between both of adjacent arch-shaped elements and the commissural posts.

Still further features of the invention provide for each arc, alternatively the haunches, to have different widths along their lengths; for the arcs of the arch-shaped elements to be thinner than the haunches thereby reducing the development of large stresses in the arcs during compressing and expanding of the stent; alternatively for the arcs and end sections of the haunches to be thicker than the remainder of the haunches to thereby evenly distribute strain within the stent and reduce peak plastic strains in the stent body and leaflets and to reduce relative movement between the leaflets and the stent.

The invention extends to a stent as described above for use in a prosthetic heart valve.

Further features of the invention provide for the stent to include biasing members capable of at least partial elastic deformation during compression of the stent and which act on adjacent haunches to bias the haunches from the compressed condition to the operative condition; for the biasing members to be located between the haunches of an arch-shaped element, or between the haunches of adjacent arch-shaped elements; alternatively for the biasing members to extend around the peaks of the commissural posts; and for the biasing members to render the stent at least partially self-expanding.

Still further features of the invention provide the stent to include locating members which extend outwardly from the body of the stent and which assist in locating the valve within the annulus of a natural heart valve.

The invention extends to a leaflet as defined above for use in a prosthetic heart valve.

Further features of the invention provide for the leaflets to be manufactured through a process of dip moulding or spray moulding.

BRIEF DESCRIPTION OF THE DRAWINGS

The invention will now be described, by way of example only with reference to the accompanying representations in which:

FIG. 12 illustrates a front view of the cylinder of FIG. 11, showing the angle θ formed by cutting the cylinder with a plane;

FIG. 13 illustrates a top view of the cylinder illustrated in FIGS. 111 and 12;

FIG. 14 is a diagrammatic illustration of a stent having reinforcing members in accordance with a first embodiment of the invention;

DETAILED DESCRIPTION WITH REFERENCE TO THE DRAWINGS

Figure 1:
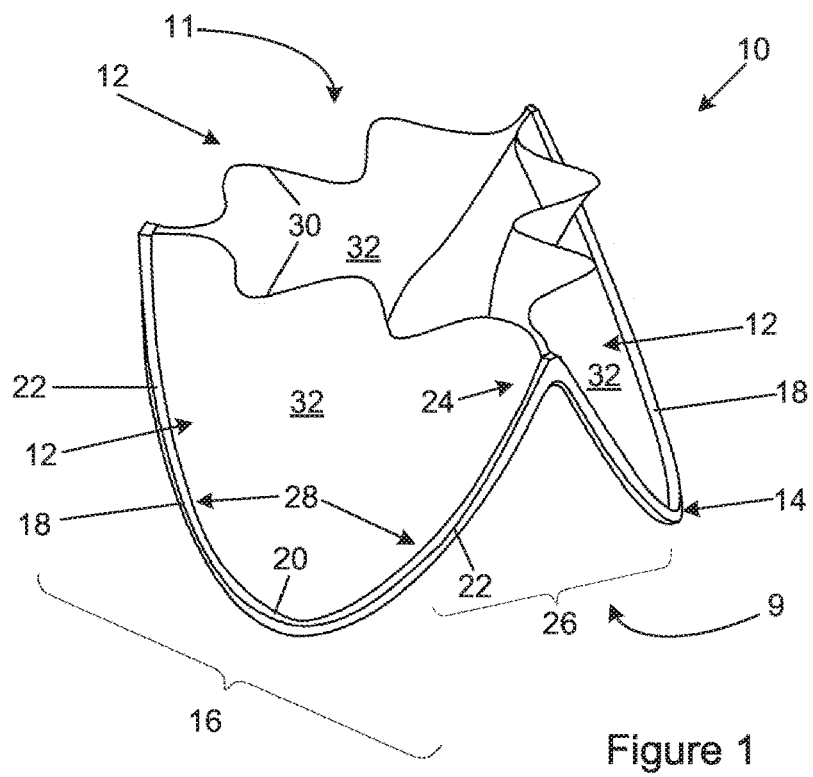
FIG. 1 illustrates a three-dimensional view of a prosthetic tri-leaflet heart valve in accordance with the invention.

FIG. 1 illustrates one embodiment of a compressible prosthetic heart valve (10) which has an inlet (9) and an outlet (11) and which includes three leaflets (12) made from a polymeric material and which are attached to a stent (14). The stent (14) is compressible to a compressed condition in which the valve (10) has a reduced diameter which permits it to be introduced into a patient's body by a minimally invasive procedure and may then be expanded from the compressed condition to an operative condition during deployment of the valve (10) within the patient's body. The stent has a ring-like body (16) defining in its height three arch-shaped elements (18), each having an arc (20) and a pair of haunches (22) that extend from opposite sides of the arc (20). The haunches (22) of adjacent arch-shaped elements (18) form three commissural post (24) of the stent having peaks (26) at ends of the haunches (22).

Each leaflet (12) has an attachment edge (28) and a free edge (30) with a belly (32) extending between the free edge (30) and the attachment edge (28). Each attachment edge (28) is continuously attached along the length of one of the arch-shaped elements (18) of the stent (14) so as to reduce the development of stress concentrations within the leaflets (12) during operation of the valve (10). In order to provide for continuous attachment of the leaflets (12) to the stent (14), the leaflets (12) are moulded directly to the arch-shaped elements (18) of the stent (14).

Figure 4:
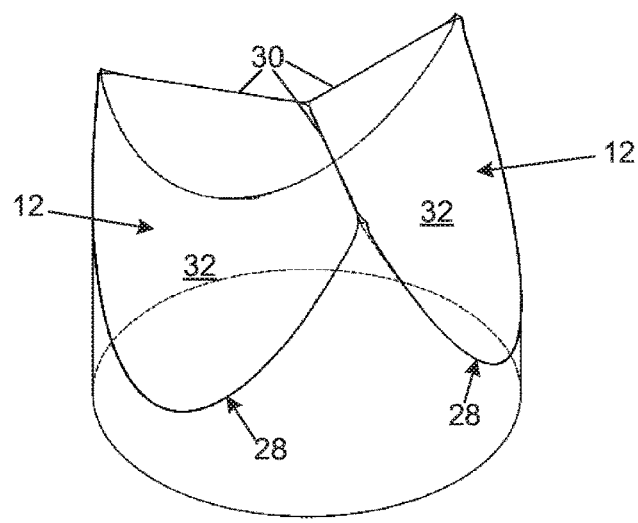
FIG. 4 illustrates a three-dimensional view of leaflets of a valve illustrated in FIG. 3, in which the leaflets are in an open condition.
Figure 3:
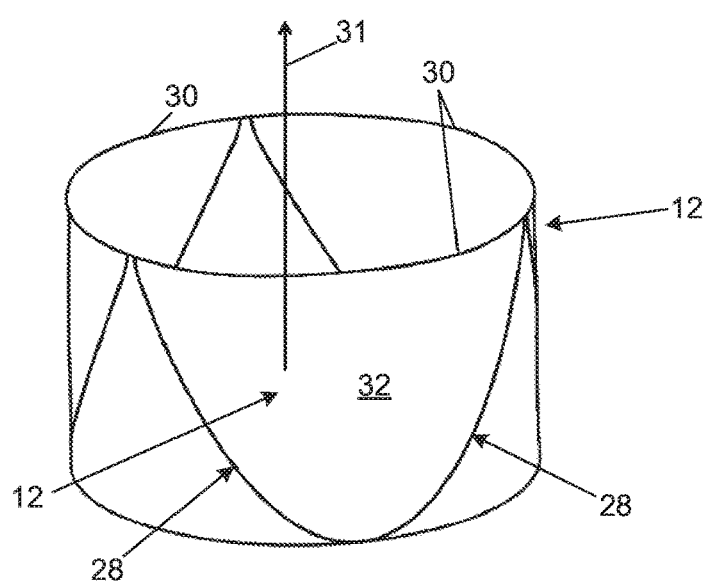
FIG. 3 illustrates a three-dimensional view of leaflets of a valve according to the invention, in which the leaflets are in a coapted condition.

During operation of the valve (10), the leaflets (12) are required to mimic natural heart valve operation and are thus movable between an open condition, in which fluid flow through the valve (10) is permitted from the inlet (9) to the outlet (11), as illustrated in FIG. 3, and a coapted (closed) condition, in which the free edges (30) abut and prevent fluid flow through the valve (10) in the opposite direction, from the outlet (11) to the inlet (9) as illustrated in FIG. 4. The directional arrow (31) in FIG. 3 shows the direction of blood flow which causes the leaflets (12) to move into the open condition.

It will be appreciated that although the arch-shaped elements (18) of the stent (14) may differ in shape from the shape of the attachment edges (28) of the leaflets (14) while maintaining continuous attachment between them, in a preferred embodiment of the invention the shape of the arch-shaped elements (18) and the shape of the attachment edges (28) are identical, thereby ensuring that the development of stresses within the leaflets (12) is kept to a minimum.

Figure 2:
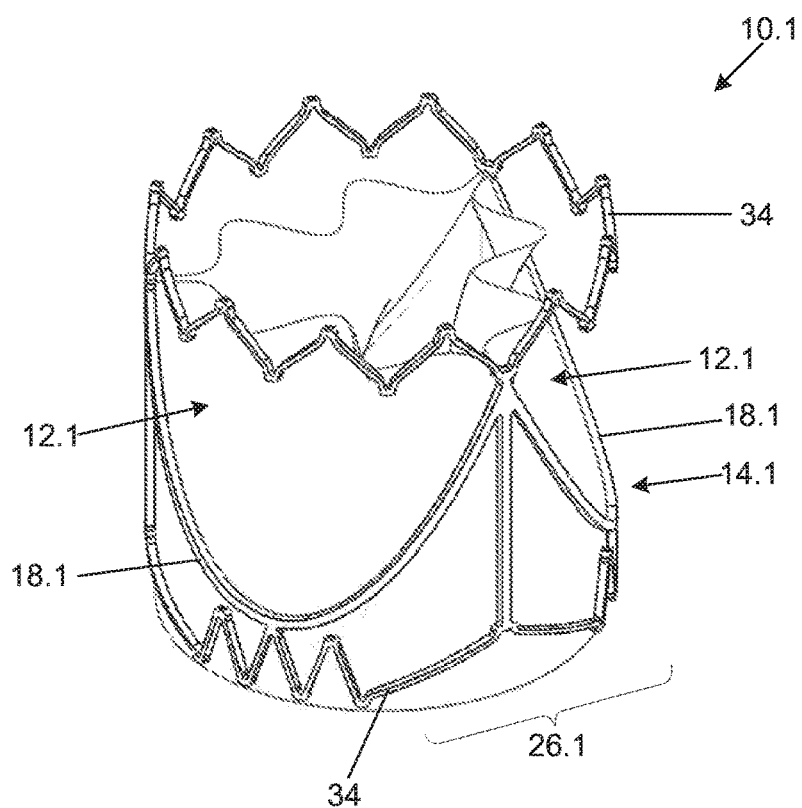
FIG. 2 illustrates a three-dimensional view of an alternative embodiment of the valve illustrated in FIG. 1, in which the stent has reinforcing members.

FIG. 2 illustrates an alternative embodiment of a valve (10.1) in which the stent (14.1) further includes reinforcing members (34) that span between adjacent arch-shaped elements (18.1) and between the commissural posts (26.1). The reinforcing members act to strengthen the stent (14.1) as well as support the leaflets (12.1) during opening and closing thereof. The reinforcing members (34) also assist in securing the valve (10.1) within the annulus of a natural heart valve. The design of the reinforcing members (34) may be varied depending on the nature and functioning of the valve (10.1), as will be described in more detail below.

Figure 5:
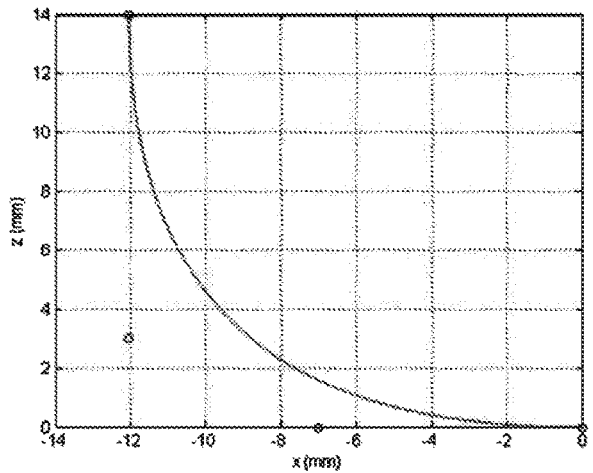
FIG. 5 illustrates a curve used for the design of an attachment edge of a leaflet in accordance with the invention.

The shape of the arch-shaped elements (18) is defined by a parametric curve in a two dimensional plane that is mirrored about the z-axis to form an arch which is wrapped about a cylinder having a diameter of the valve (10). The parametric curve is preferably defined by a function (the "arc function") $A(x)=(1-x)^3 xP_0+3(1-x)^2 P_1+3(1-x)x^2 P_2+x^3 P_3$, with $P_0$ to $P_3$ being control points that may be varied so as to optimize the curvature of the curve. FIG. 5 illustrates how the parametric curve may be utilized to draw half of an arch-shaped element in an x-z plane, which may then be wrapped about a cylinder so as to result in the shape of half of an arch-shaped element (18). The resulting half of the arch-shape is mirrored about the z-axis to thereby form an arch, which is then wrapped about the cylinder.

The control points $P_0$ and $P_3$ are preferably selected on the basis of the diameter and height of the valve (10) respectively, while $P_1$ is preferably selected from the range of $0 \leq z \leq H$ and $P_2$ is selected from the range $0 \leq x \leq \pi D/6$ with H being the height and D the diameter of the valve (10). In that regard, the curve illustrated in FIG. 5 is generated by setting $P_0$ equal to the valve height, being 14 millimetres, $P_3$ equal to one sixth of the circumference of the valve and then varying $P_1$ and $P_2$ until an optimum curvature is achieved, in the embodiment illustrated in FIG. 4 by setting $P_1$ equal to 3 millimetres and $P_2$ equal to 7 millimetres.

Figure 6:
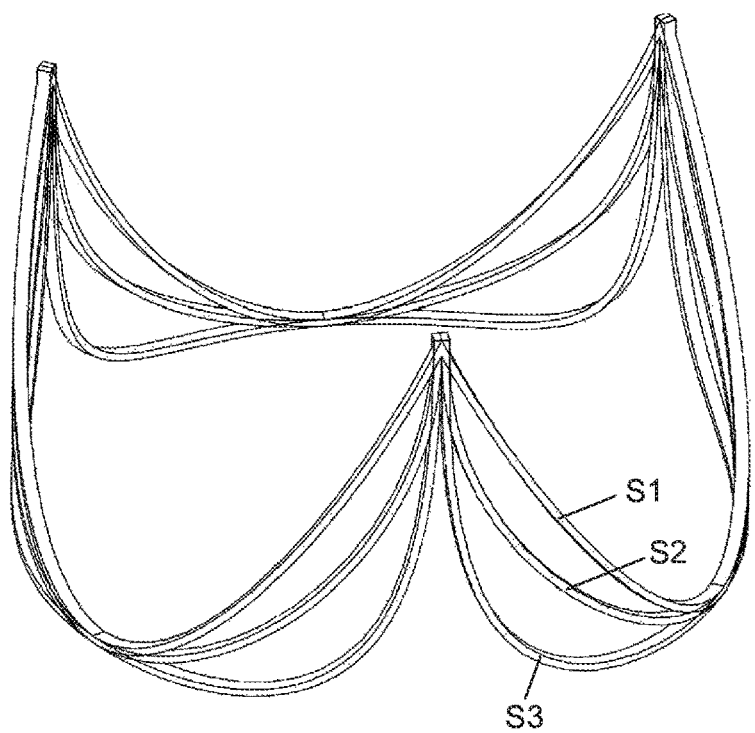
FIG. 6 illustrates a three-dimensional view of a plurality of arch-shaped elements obtainable through variation of design parameters in accordance with the invention.

The variation of the values selected for $P_1$ and $P_2$ as described above, enables the generation of a plurality of differently shaped stents, of which three are illustrated in FIG. 6 numbered S1 to S3, having smooth and continuously shaped arch-shaped elements (18) as is illustrated. As the shape of the arch-shaped elements (18) influences the mechanical behaviour of both the leaflets (12) and the stent (14), it is important that the shape of these elements is optimized so as to allow the stent (14) to be compressed when the valve (10) is being introduced into a patient's body, while at the same time retaining the stent's mechanical properties so as to keep the development of stresses during opening and closing of the leaflets (10) to a minimum. It has been found that the optimum shape of an arch-shaped element (18) is achieved when $P_1$ is selected from the range of $0.3H \leq z \leq 0.5H$ and $P_2$ from the range of $0.4(\pi D/6) \leq x \leq 0.6(\pi D/6)$. This ensures that the arch-shaped elements (18) of the stent (14) do not have a flat arc (20), which would result in high stresses in the arcs (20) during compressing of the stent (14), while at the same time ensuring that the development of stresses in the leaflets (12) during opening and closing is kept to a minimum.

Figure 7:
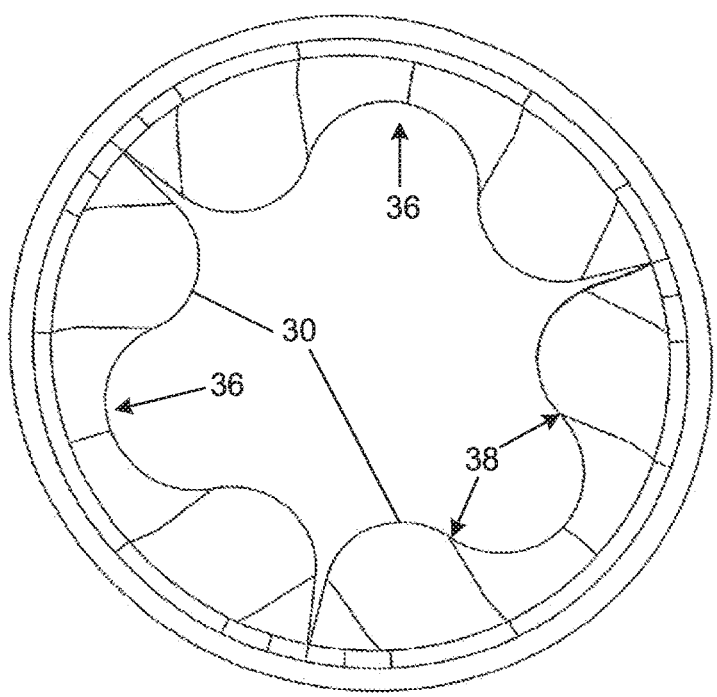
FIG. 7 illustrates a top view of a prosthetic heart valve of the prior art, in which the leaflets are in a partially open condition.

Furthermore, in a preferred embodiment of the invention, the free edge (30) of each leaflet (12) has a minimum length that is greater than twice the radius of the valve (10) so as to ensure proper coaptation of the leaflets (12) during operation of the valve (10). Defining a free edge (30) to have a length greater than twice the radius of the valve (10) will result in the free edges (30) forming bends (36) along their length when in the open condition, as is illustrated in FIG. 7. Although the bends (36) will be necessary to provide the required length of free edge (30) to ensure proper coaptation, these result in high stresses at the points of inflection (38) where the free edge (30) is too long.

In order to keep stresses at the bends (36) to a minimum, while at the same time providing for proper coaptation, it is preferred that the free edges (30) are defined by the following three functions (the "free edge functions"):

$$y = mx \text{ for } -c_b \leq x < -c_b + x_s$$

$$y = K \cos(Lx) + t \text{ for } -c_b + x_s \leq x < c_b - x_s$$

$$y = -mx \text{ for } c_b - x_s \leq x \leq c_b$$

where $c_b$ is defined as end-points of the free edge. The variable $x_s$ is a function of the straight line portion of the free edge where the free edge is secured to the commissural posts, and may vary according to the leaflet design. The straight line portion of the free edge (30) will reduce the degree of folding of the leaflet adjacent the commissural posts (26), thereby reducing the development of stresses in those areas while also reducing the possibility of blood coagulation in those areas. It will also reduce pooling of the polymer at the commissural posts during manufacture of the valve.

The constant m should be in the range of 0.1 to 1, preferably in the range of 0.3 to 0.8, and more preferably in the range of 0.55 to 0.75. The constant K should be in the range of −3 to 0, preferably in the range of −3 to −2, and more preferably in the range of −2.7 to −2.3. The constant L should be in the range of 0.05 to 1.5, preferably in the range of 0.2 to 1, and more preferably in the range of 0.5 to 0.6. The constant t is such that it ensures the end points of the curves provided by the three equations above always meet one another.

In order to smoothen the junctions between the different curves provided by the three equations above, a fillet of radius Rf may be added. This constant should be in the range of 0.5 to 3, preferably in the range of 0.5 to 1.5, and more preferably in the range of 0.8 to 1.2.

Figure 8:
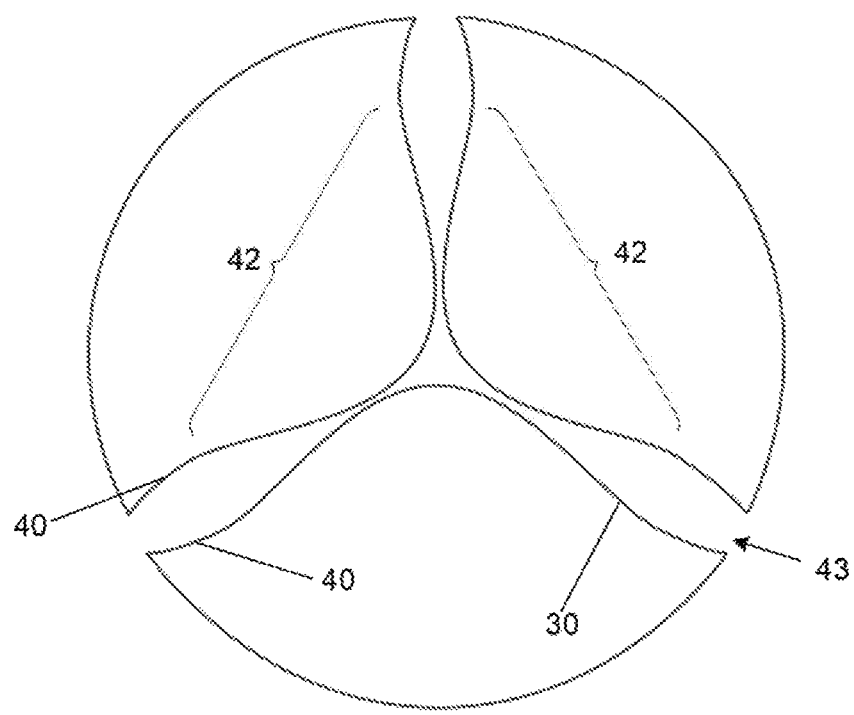
FIG. 8 illustrates a top view of a leaflet in accordance with the invention.

Designing of the free edges (30) in this way will result in the free edges (30) having straight lines at the ends (40) thereof with a cosine function defining the central section (42) of the free edge (30), as is illustrated in FIG. 8. In addition, it is preferred that the free edges (30) are designed such that they do not meet and thus form a gap (43) which will prevent the free edges (30) from tearing during opening and closing of the leaflets (12). Also, the straight lines at the ends (40) of the free edge (30) assists in keeping to a minimum the stresses, which may develop in the leaflet (12) at the commissural posts (26).

Further, in this embodiment the free edge of each leaflet is of a length equal to or greater than an arc of radius R between the two points on the attachment edge where the free edge intersects (extends from) the attachment edge, where R is the radius of the valve. The free edge of each leaflet should also be equal to or greater than the length of an element spanning between two commissural posts and which is folded inward to the centre of the valve, thereby forcing a closed or coapted portion of the leaflets. Furthermore, the height of the valve should always be greater than the radius of the valve.

In addition to the design of the arch-shape and the free edge (30) as set out above, the belly (32) of a leaflet (12) is preferably defined by a parametric curve in a two dimensional plane, with the parametric curve being defined by a function (the "belly function") $B(x) = (1-x)^3 P_0 + 3(1-x)^2 x P_1 + 3(1-x)x^2 P_2 + x^3 P_3$, with $P_0$ to $P_3$ being control points. Control points $P_2$ and $P_3$ preferably remain constant, while $P_0$ is selected from the range of $0.3D \leq P_{0x} \leq 0.5D$ and $0.5H \leq P_{0y} \leq 0.8H$ and $P_1$ is selected from the range $0.4D \leq P_{1x} \leq 0.6D$ and $0.3H \leq P_{1y} \leq 0.8H$ with H being the height and D the diameter of the valve (10). The use of the parametric curve and optimization of control points for $P_0$ to $P_1$ ensures that the leaflets (12) properly coapt and open during operation of the valve (10), thereby ensuring that proper blood flow is not prevented and that no regurgitation takes place, but also keep the development of stresses in the leaflets (12) to a minimum.

The design of the leaflets (12) as described above ensures that when the leaflets (12) are fully opened, the free edges (30) closely approximate the profile of a cylinder of the specific valve (10) radius. This, in turn, leads to a valve (10) with a low pressure drop which results in improved haemodynamic performance.

Furthermore, by defining the length of the free edges (30) exactly, a redundancy may be incorporated in the length of the free edges (30) which will allow the leaflets (12) to still close fully when the valve (10) is over-deployed, that is, expanded to a greater diameter during deployment than the one it was designed for.

It will be appreciated that the designs of the arch-shape, the free edge and the belly as described above generally provide for the generation of single line curves only, thus in order to produce the full leaflet shape having the desired features, a surface is lofted or meshed between the individually designed curves. This process is known in the art.

The prosthetic heart valve (10) described above may be manufactured in a one-step process by moulding the leaflets (12) directly onto the stent (14). Alternatively, the valve (10) may be manufactured in a two-step process by first moulding the leaflets (12) and then attaching them to the stent (14)

through a second moulding process. However, it is preferred that the leaflets (12) are pre-moulded to an intermediate thickness and the pre-moulded leaflets (12) are then moulded directly onto the stent (14). This ensures that the attachment edge (28) of each leaflet (12) is continuously attached along the length of an arch-shaped element (18). Furthermore, in this preferred method, the stent (14) is pre-coated with the same or similar polymeric material from which the leaflets (12) are pre-moulded, before the leaflets (12) are moulded thereon. During moulding of the leaflets (12) onto the stent (14), the thickness of the leaflets (12) is increased to a desired final thickness. This process ensures that the leaflets (12) are properly attached to the stent (14) along the attachment edge (28) by fully encapsulating the arch-shaped elements (18) with the polymeric material. During the moulding process, particularly during a spray moulding process, the entire stent (18) may be encapsulated, alternatively masking techniques may be used to selectively coat certain parts of the stent (14).

Figure 9:
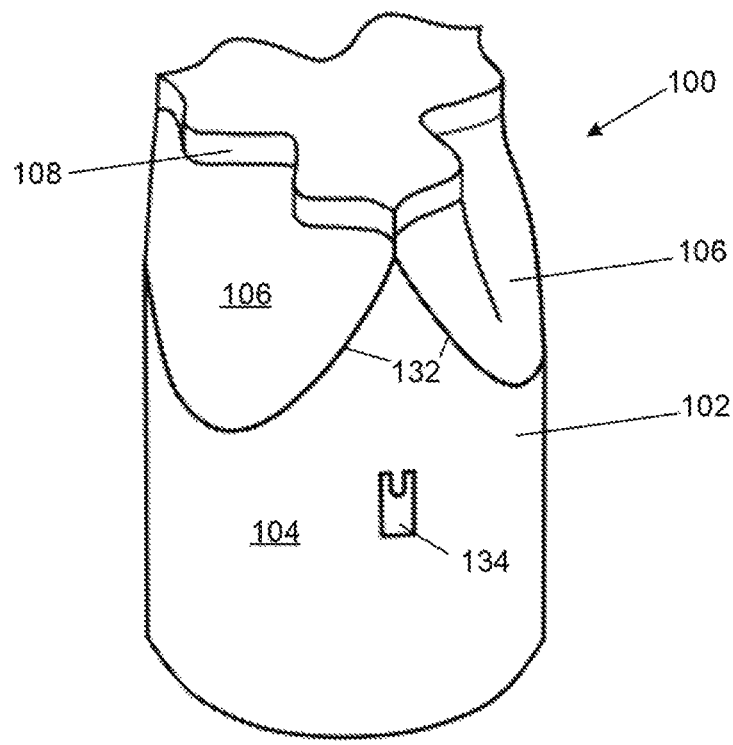
FIG. 9 illustrates a three-dimensional view of a spray coating mould for manufacturing leaflets in accordance with the invention.
Figure 10:
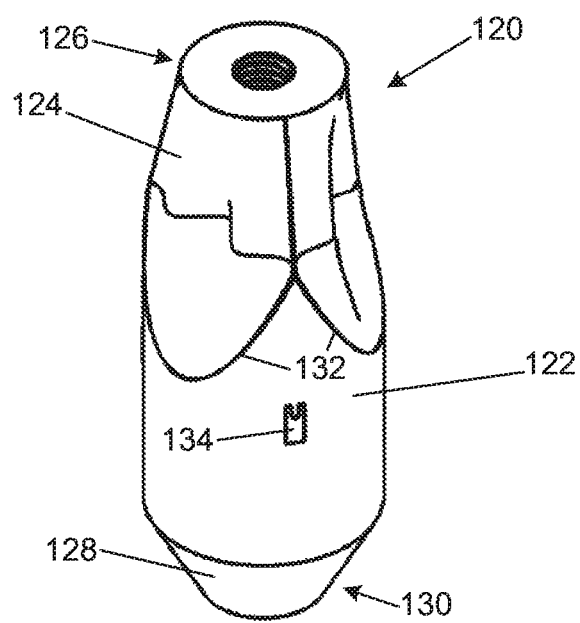
FIG. 10 illustrates a three-dimensional view of a dip coating mould for manufacturing leaflets in accordance with the invention.

FIG. 9 illustrates a mould (100) that may be used for a spray coating process, while FIG. 10 illustrates a mould (120) that may be used for a dip coating process.

The moulds (100, 120) may be manufactured from any suitable material, including metal, wood, polymer and glass. The outer surface (102, 122) of the mould (100, 120) may, in some embodiments, also be coated with any appropriate material so as to enhance desired surface properties of the mould (100, 120).

The spray coating mould (100) of FIG. 9 has a body portion (104) and three leaflet portions (106) integral with the body portion (104). These are designed so as to provide the leaflets (12) with the properties as described above. The mould (100) further includes a top portion (108) which provides additional height to the mould (100) and thus results in the leaflets (12) having an increased height so as to ensure that the leaflets (12) will have excess height when removed from the mould (100). Once the leaflets (12) have been removed, the free edges (30) may be cut from the moulded leaflets (12) by means of a blade, razor or a laser, but any other method may be used, so as to ensure that the leaflets (12) have the desired free edge (30) length as described above.

In order to manufacture the leaflets (12), the mould (100) may be rotated horizontally about a longitudinal axis and then sprayed with a polymer solution. The polymer solution is allowed to dry on the mould (100) while still rotating or being supported in specified configurations or being manoeuvred in any three-dimensional pattern. This process may be repeated several times until a desired leaflet (12) thickness is achieved.

Spraying can take place in ambient conditions. However, it is preferable to spray the mould (100) in a chamber or oven in which the temperature and humidity are controlled. The temperature in such a chamber would preferably be in the range of 0° C. to 150° C., more preferably in the range of 10° C. and 60° C. and more preferably in the range of 15° C. and 30° C., and the humidity in such a chamber would be in the range of 0% to 100% relative humidity, preferably in the range of 0% to 50% relative humidity, and more preferably in the range of 5% to 20% relative humidity. The mould (100) may be sprayed in a chamber which is substantially free of oxygen in order to avoid the oxygen from interacting with the polymeric material. Spraying may, however, also take place in a solvent rich environment.

Solvents for spraying may be organic solvents, such as dimethyl acetamide (DMAC), tetrahydrofuran (THF), cyclohexanone, toluene, dimethyl formamide (DMF), but inorganic solvents may also be used. In a preferred embodiment, dimethyl acetamide is used as a solvent due to its diprotic nature and good solvability of the polymer. Furthermore, when using DMAC as a solvent, it is preferred that the spraying takes place in a low humidity environment to prevent phase inversion.

Drying can take place in ambient conditions. However, it may be preferable to dry the coated mould (100) in a chamber or oven in which the temperature and humidity are controlled. The temperature ranges in such a chamber are preferably in the range of 0° C. to 150° C., more preferably in the range of 30° C. to 100° C. and most preferably in the range of 50° C. to 70° C. The coated mould (100) may also be dried in a chamber which is substantially free of oxygen to avoid oxygen interaction with the polymer. The humidity ranges in such a chamber are preferably in the range of 0% to 100% relative humidity, more preferably in the range of 0% to 50% relative humidity, and most preferably in the range of 5% and 20% relative humidity.

The polymer solution sprayed onto the mould may contain a relatively low concentration of polymeric material. The concentrations of the solutions used will depend on the viscosity of the solutions used, which in turn will depend on the molecular weight of the polymer and the solubility of the polymer in the chosen solvent. The solution concentration is preferably between 1% and 10% (m/m), more preferably between 2% and 8% (m/m), and most preferably between 3% and 6% (m/m). It has been found that these concentrations ensure proper atomisation of the solution and eliminate the occurrence of webbing.

In one embodiment of the invention, a polymer solution is sprayed onto the mould (100). Spraying time will preferably be between 1 second and 20 minutes, more preferably between 5 and 30 seconds, and most preferably between 5 and 10 seconds, depending on the volume of solution sprayed onto the mould (100). The mould (100) is sprayed while it is rotating horizontally, and then left to dry while still rotating, until all of the solvents have evaporated from the polymer film. The drying may take place in a convection oven with the mould (100) in a known fixed position or while rotating around an axis or while being maneuvered in any three-dimensional pattern. The mould (100) could, however, also be dried in a chamber in which the environment, particularly temperature and relative humidity, can be controlled. The drying may take 5 to 20 minutes, but could take for as long as an hour in order to ensure that even trace amounts of solvents are evaporated, depending on the solvent used and the volume sprayed. Once completely dried, the process is repeated until the desired leaflet (12) thickness is achieved.

Spray coating in this manner has been found to produce highly uniform leaflets, particularly as the rotation during spraying and drying prevents the formation of droplets on the leaflets (12).

It will be appreciated that various other methods of spray coating may be employed without departing from the scope of the invention. For example, the mould (100) may be sprayed while it is rotated in a vertical or inclined position. Alternatively, the mould (100) may remain in a fixed position while a spraying device is moved relative to the mould (100) in order to carry out the spraying operation, or both the mould (100) and spraying device moved at the same time.

The dip coating mould (120) shown in FIG. 10 includes inwardly tapered run-offs at either end of the mould (120). A leaflet run-off (124) is provided at the end (126) of the mould (120) defining the free edges (30) of the leaflets (12)

and a base run-off (128) is provided at the end (130) of the mould (120) adjacent the attachment edges (28) of the leaflets (12).

The run-offs (124, 128) act to prevent pooling of a polymer solution which can take place while the polymer solution is allowed to dry on the mould (120) after dip coating in the polymer solution. The solution's concentration should preferably be in the range of 5% to 40% (m/m), more preferably in the range of 10% to 30% (m/m), and most preferably in the range of 10% to 20% (m/m). Typically, the mould (120) is hung with either the free edge (30) end facing downward or the attachment edge (28) side facing downward, depending on the run-off configuration. Alternatively, the mould (120) can be made to stand on one of its ends (126, 130) on a surface during drying, however, drying may of course take place in any other suitable manner, such as while maneuvering in any three-dimensional pattern. The drying of the polymeric film may also take place in an oven or a chamber in which the environment can be controlled, however, it may also take place at ambient conditions depending on the solvent used. Temperature ranges for drying could be between 0° C. and 150° C., but more preferably between 30° C. and 100° C., and most preferably between 50° C. and 70° C. After the mould (120) has been dipped in a polymer solution, the polymer solution flows under gravity down the mould (120) and pools at the lowermost end. The run-offs (124, 128) ensure that the polymer solution is diverted away from the ends (126, 130) of the mould (120) defining the leaflets (12). The resultant leaflets (12) have been found to have excellent uniformity, particularly because the run-offs (124, 128) reduce pooling at the attachment edge (28), the free edge (30) and folds or bends of the leaflet belly (32) to thereby provide an even leaflet (12) thickness.

Either end (126, 130) of the mould (120) can be used to support the mould (120) during drying, and it is often desirable to use alternate ends after each dip coating to ensure an even distribution of the polymer solution on the mould (120).

The taper angle of the leaflet run-off (124) areas is between 25 and 90 degrees, preferably between 55 and 90 degrees. The taper angle of the base run-off (128) is between 25 and 90 degrees, preferably between 45 and 55 degrees. The taper angles and other dimensions of the run-off areas can, however, be altered to achieve a desired valve thickness taking into account the properties of the polymer solution used.

To ensure that the leaflets (12) are not damaged or torn when removed from the moulds (100, 120), the moulds (100, 120) may further be provided with rounded edges (110, 132) in the areas defining the leaflets.

The moulds (100, 120) can also be provided with a stent (14) holder for securing a stent on an outer surface thereof in the correct orientation relative to the leaflets (12). In the embodiments illustrated in FIGS. 9 and 10, the moulds (100, 120) include a number of clip formations (112, 134) about the mould (100, 120). These facilitate securing the stent (14) on the mould prior to or during polymer coating so that the stent (14) is also coated with the polymer. This ensures that the attachment edge (28) is continuously attached along the length of an arch-shaped element (18). To this end, the clip formations (112, 134) maintain the stent (14) a distance of between 0 millimetres and 0.25 millimetres from the surface (102, 122) of the mould (100, 120).

It will be appreciated that due to the dip coating mould (120) allowing for the mould (120) to be dipped in either direction during manufacture of the leaflets (12) and valve (10), the need for cutting of the free edges (30) may be eliminated, thus ensuring that the final dimensions accurately correspond to the leaflet (12) design. Furthermore, the run-offs (124, 128) of the mould (120) may be altered to control the thickness distribution of the leaflet (12).

Figure 11:
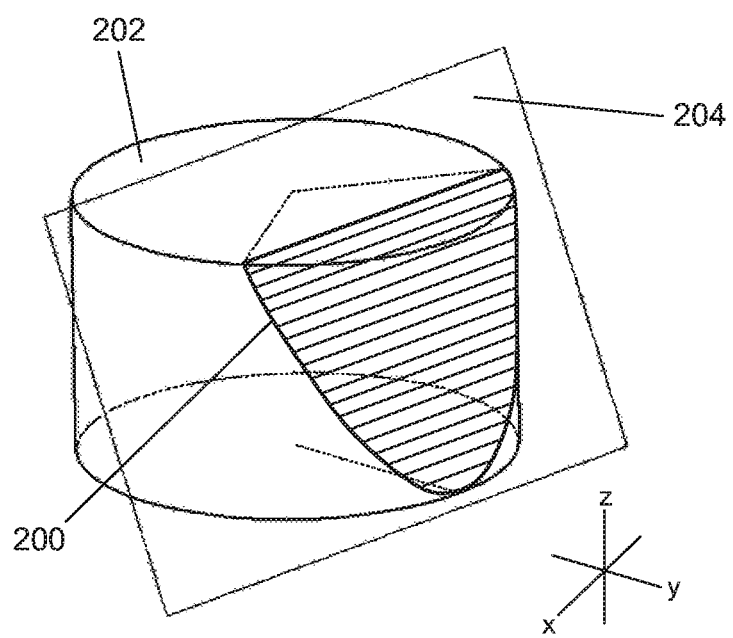
FIG. 11 illustrates a three-dimensional view of one embodiment of designing an arch-shape by cutting a cylinder with a plane at an angle θ.

It will further be appreciated that the design of the arch-shape, free edge and belly may be changed substantially while maintaining the desired properties of the leaflets and stent. Thus, in one alternative embodiment of the invention, the arch-shape can be defined by a plane, cylinder or cone intersecting a cylinder or cone at an angle theta (8). FIGS. 11 and 12 illustrate the arch-shape (200) provided by cutting a cylinder (202) with a plane (204) at an angle theta (8). The angle θ is dependent on the height and radius of the prosthetic heart valve.

FIG. 13 shows a top view of the cylinder of FIG. 12. An angle phi (φ), where 2φ is defined as the central arc angle formed by radii extending to each of the two points on the attachment edge (28) where the free edge (30) of the leaflet (12) intersects the attachment edge (28), and is dependent on the height and radius of the valve. The height and radius of the valve are illustrated in FIG. 12. The dependency on the height and radius of the valve leads to a tangent of the angle θ which is equal to (R−R cos(θ))/H, where R is the radius and H the height of the valve.

In yet a further embodiment of the invention, the arch-shape can be defined by the following set of parametric arc functions:

$$x = R\sin(t)$$
$$y = R\cos(t)$$
$$z = \frac{D - BR\cos(t)}{C}$$

where R is the inner radius of the valve and B, C and D are constants obtained in determining the equation of the plane which cuts the cylinder. The parameter t is varied and spans a range of 0 to 2π/3 for one leaflet.

The result of these equations is that the arch-shape follows a circular path of radius R in the x-y plane, a parabola-like shape in the x-z plane, and an inclined straight line in the y-z plane.

In still a further embodiment of the invention, the arch-shape can be defined by a three-dimensional sinusoidal curve. In this embodiment, the arch-shape can thus be defined by the following set of parametric arc functions:

$$x = R\sin(t)$$
$$y = R\cos(t)$$
$$z = \frac{J}{2}\sin(3t) + \frac{J}{2}$$

where R is equal to the valve radius and J is equal to the valve height. The parameter t is varied and spans a range of 0 to 2π/3 for one leaflet.

It should also be noted that the free edge of the leaflet may be defined in various ways. For example, in one embodiment of the invention, the free edge of the leaflet (12) may be defined by a function y=−E cos(Fx)(G cos(Hx)+G/2) with the constant E being in the range of 0.5 to 2.5, preferably in the range of 1 to 2, and more preferably in the range of 1.2 to 1.6. The constant F should be in the range of 0.05 to 1, preferably in the range of 0.05 to 0.5, and more preferably in the range of 0.1 to 0.2. The constant G should be in the range of 0.5 to 2.5, preferably in the range of 1 to 2.5, and more preferably in the range of 1.5 to 2. Finally, the constant H should be in the range of 0.05 to 1.5, preferably in the range of 0.2 to 1, and more preferably in the range of 0.6 to 0.7. In still a further embodiment of the invention, the free edge of each leaflet may be defined by the following equations:

$$y = P\cos(Qx) + S\cos(Tx) - v$$

$$y = U\cos(Tx)(P\cos(Qx) + S\cos(Tx)) - v$$

where constant P should be in the range of 0.2 to 1.5, preferably in the range of 0.4 to 0.8, and more preferably in the range of 0.6 to 0.7. The constant Q should be in the range of 0.5 to 3.5, preferably in the range of 1.5 to 2.5, and more preferably in the range of 2.1 to 2.25. The constant S should be in the range of 0.1 to 0.5, preferably in the range 0.15 to 0.3, and more preferably in the range of 0.23 to 0.26. The constant T should be in the range of 0.05 to 0.3, preferably in the range of 0.1 to 0.2, and more preferably in the range of 0.15 to 0.18. The constant U should be in the range of 0.5 to 3, preferably in the range of 1 to 2, and more preferably in the range of 1.2 to 1.3. The value v is calculated such that the end points of the curve always intersect the points having the following coordinates when plotted on a graph (−R sin(π/3); R cos(π/3)) and (R sin(π/3); R cos(π/3)).

In this embodiment, the end points of the free edge may be rounded to allow better opening characteristics at the commissural posts and also to ease manufacturability of the leaflets. The rounding can be achieved by replacing data points at the edge of the cosine function with the data points of a quarter circle of radius Rc. The value of Rc should be in the range of 0.05 to 1, preferably in the range of 0.2 to 0.8, and more preferably in the range of 0.45 to 0.55.

The curves of this embodiment are fitted between two commissure boundaries. A first commissure boundary is defined as the point where a line of length R (the radius of the valve), drawn at an angle of 30 degrees with the horizontal would intersect a circle of radius R. A second commissure boundary lies 120 degrees from that point on a circle of radius R. A third commissure boundary then lies another 120 degrees from that point. The x and y coordinates of the first commissure point would then be (R cos θ; R sin θ).

Similarly to the different arch-shape and free edge definitions above, the belly extending between each free edge and attachment edge may be defined in different ways. For example, in one embodiment of the invention, the belly may be defined by:

$$z = \left(A_b e^{-\frac{(y-\mu)^2}{2\sigma^2}}\right)(-A_c \cos(B_c y) + A_c)$$

The constant $A_b$ should be in the range of 1 to 10, preferably in the range of 4 to 8, and more preferably in the range of 6.5 to 7.5. The constant μ should be in the range of 5 to 10, preferably in the range of 7 to 9, and more preferably in the range of 7.8 to 8.3. The value of μ is dependent on the length of the belly curve and has a direct relation to that length.

The constant σ should be in the range of 10 to 15, preferably in the range of 11 to 13, and more preferably in the range of 12 to 12.5. The constant $A_c$ should be in the range of 0.1 to 0.6, preferably in the range of 0.3 to 0.5, and more preferably in the range of 0.33 to 0.4. Constant $B_c$ is in the range of 0.25 to 0.5, preferably in the range of 0.3 to 0.45, and more preferably in the range of 0.35 to 0.4. The value of $B_c$ is also dependent on the length of the belly curve.

In yet a further embodiment of the invention, the belly may be defined by:

$$z = \left(A_b e^{-\frac{(y-\mu)^2}{2\sigma^2}}\right)(-A_c \sin(B_c y))$$

The constant $A_b$ should be in the range of 1 to 5, preferably in the range of 2 to 4, and more preferably in the range of 3 to 3.5. The constant μ should be in the range of 10 to 20, preferably in the range of 12 to 16, and more preferably in the range of 14.5 to 15.5. The value of μ is dependent on the length of the belly curve and has a direct relation to that length.

The constant σ is in the range of 5 to 10, preferably in the range of 7 to 9, and more preferably in the range of 7.5 to 8.5. The constant $A_c$ should be in the range of 0.5 to 5, preferably in the range of 1 to 3, and more preferably in the range of 1.5 to 2.5. The constant $B_c$ should be in the range of 0.05 to 0.3, preferably in the range of 0.1 to 0.25, and more preferably in the range of 0.15 to 0.2. The value of $B_c$ is also dependent on the length of the belly.

Again, as set out above, it will be appreciated that the various designs of the arch-shape, the free edge and the belly as described above generally provide for the generation of single line curves only, thus in order to produce the full leaflet shape having the desired features, a surface is lofted or meshed between the individually designed curves, as is known in the art.

It will further be appreciated that the stent can have many suitable shapes and can be made from any suitable material such as stainless steels, alloys of cobalt, chromium, molybdenum, or nickel, or from shape-memory and superelastic materials such as nickel titanium (Nitinol), or from titanium alloys, gold, platinum-iridium, niobium alloys, palladium or tantalum, or from polymeric materials.

The reinforcing members of the stent may also vary significantly in terms of structural configuration. For example, the reinforcing members may be one or more parallel struts spaced along the length of the commissural posts or one or more curved struts spaced along the commissural posts. The struts or other reinforcing members may, in other embodiments, be concertina-shaped or diamond-shaped. The parallel, curved, concertina-shaped or diamond-shaped members may also be attached to the stent so as to span between the haunches of one or more arch-shaped elements. In a yet further embodiment, the stent includes reinforcing members providing one or more locking arrangements.

In yet another embodiment, the stent may further include reinforcing members that act as locating members and assist in correctly locating the stent within the cusps of the natural heart valve during deployment of the valve. The locating members are typically loops or arms configured to be deployed into a position wherein the loops or arms extend beyond the expanded condition of the stent. This allows the stent to be located within the cusps of the natural heart valve, thereby ensuring that the valve is expanded and deployed in a desired location relative to the natural heart valve.

In a preferred embodiment of the invention, the stent is compressible into a compressed condition so as to be capable of being introduced into a patient's body through a minimally invasive procedure. Once in position in the body the stent is expandable from the compressed condition to an operative condition. This allows the valve to be introduced into a patient's body in the compressed condition, and then expanded, or deployed, or allowed to expand, into the operative condition in order to secure the valve in the annulus of the natural heart valve.

FIGS. 14 to 18 illustrate variations of reinforcing members that may be incorporated in the stent, and which provide annular support to the stent. The illustrated reinforcing members extend between the haunches of adjacent arch-shaped elements but they could also extend within each arch-shaped element between the haunches. FIG. 14 shows a stent (300) having five struts which are outwardly curved along their length extending between adjacent haunches and spaced apart along the lengths thereof as reinforcing members (302). The reinforcing members (302) can typically be integrally formed with the haunches, for example, by cutting the entire stent (300) from a suitable material as described above, or by various other methods that are well known to those skilled in the art. It should be appreciated that any number of struts may be used for the purpose of reinforcement, and that the struts may be spaced apart in various ways.

Figure 15:
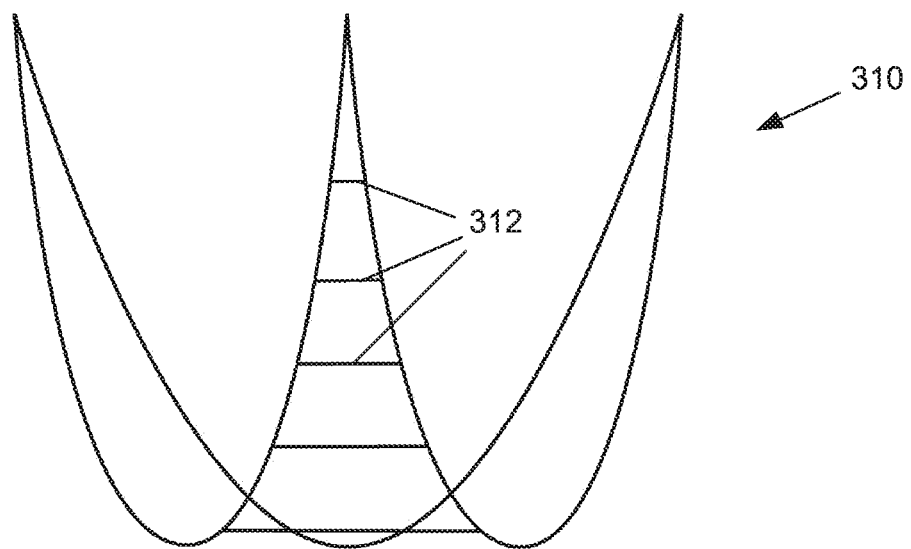
FIG. 15 is a diagrammatic illustration of a stent having reinforcing members in accordance with a second embodiment of the invention.

FIG. 15 illustrates a stent (310) of generally similar structural configuration to the stent (300) of FIG. 14. In this embodiment, parallel reinforcing members (312) extend between adjacent haunches and are spaced apart along the lengths of the haunches, but do not follow the curvature of the ring-like shape of the stent.

Figure 16:
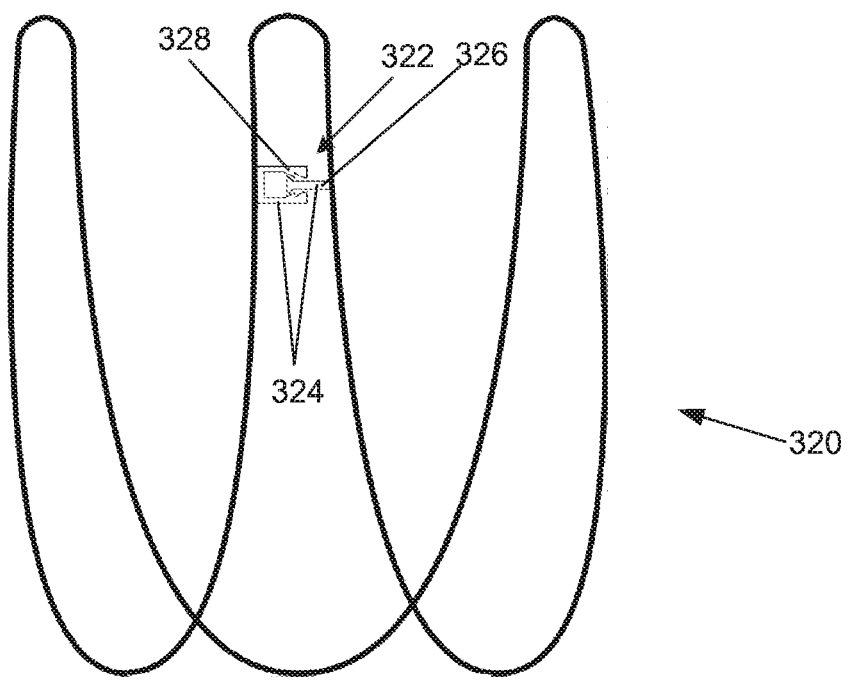
FIG. 16 is a diagrammatic illustration of a stent having locking formations in accordance with a first embodiment of the invention.
Figure 17:
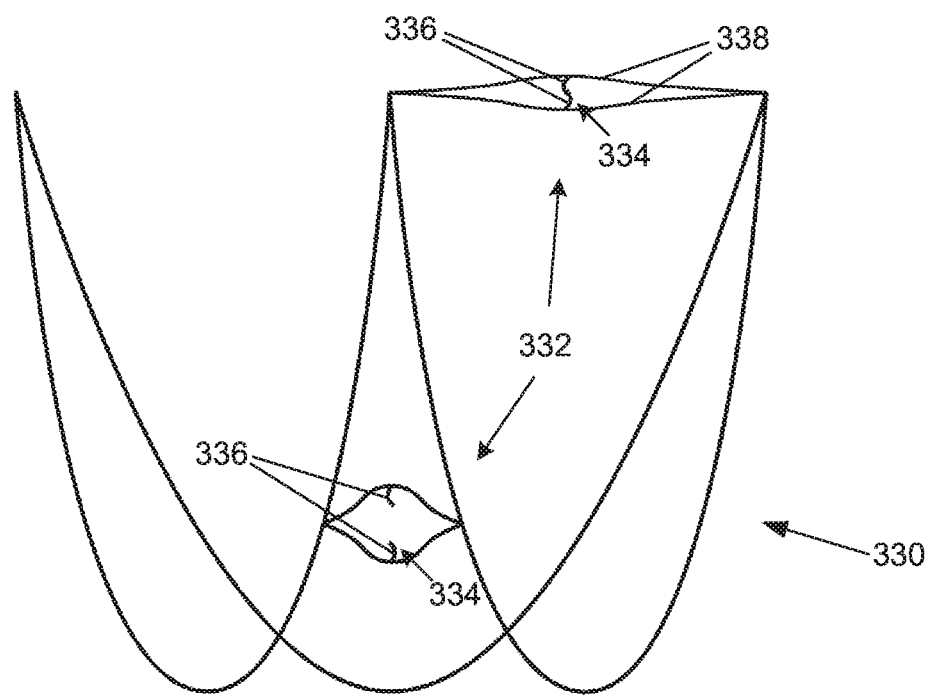
FIG. 17 is a diagrammatic illustration of a stent having locking formations in accordance with a second embodiment of the invention.

The stents (320, 330) illustrated in FIGS. 16 and 17 include reinforcing members (322, 332) which have locking mechanisms (324, 334). These locking mechanisms serve to hold the stent in the expanded condition once it has been deployed. Primarily, the locking mechanisms (324, 334) reduce recoil and provide support upon opening.

The locking mechanism (324) in the stent (320) of FIG. 16 includes a spigot (326) which extends from one of a pair of adjacent haunches and a socket (328) which extends from the other haunch. Complementary toothed formations are provided on the outer surface of the spigot (326) and inner surface of the socket (328). Expansion of the stent causes the spigot (326) to engage within the socket (328) and the toothed formations prevent the spigot (326) from being withdrawn from the socket (328) once inserted.

When the stent (320) is in the compressed condition, the spigot (326) is loose within the socket (328). When the stent (320) is expanded, the spigot (326) slides within the socket (328) until the teeth on the spigot (326) engage the teeth on the socket (328), in order to lock the stent into an expanded condition.

The locking mechanism (324) may also be elastic or partially elastic so as to limit the expansion of the stent (320) from the compressed condition, or to allow the stent (320) to be only partially expanded from the compressed position. A plurality of locking mechanisms (324) may be provided on one stent (320).

The locking mechanism (334) of the stent (330) shown in FIG. 17 includes a pair of complementary hooks (336) carried on each of a pair of bowed elements (338) extending between adjacent haunches. The locking mechanism (334) is arranged such that expansion of the stent (330) causes the bowed elements (338) to move together and the hooks (336) to engage and resist the bowed elements (338) moving apart again. This ensures that, once expanded, the stent (330) remains in the expanded condition, and also provides structural support to the stent (330).

Figure 18:
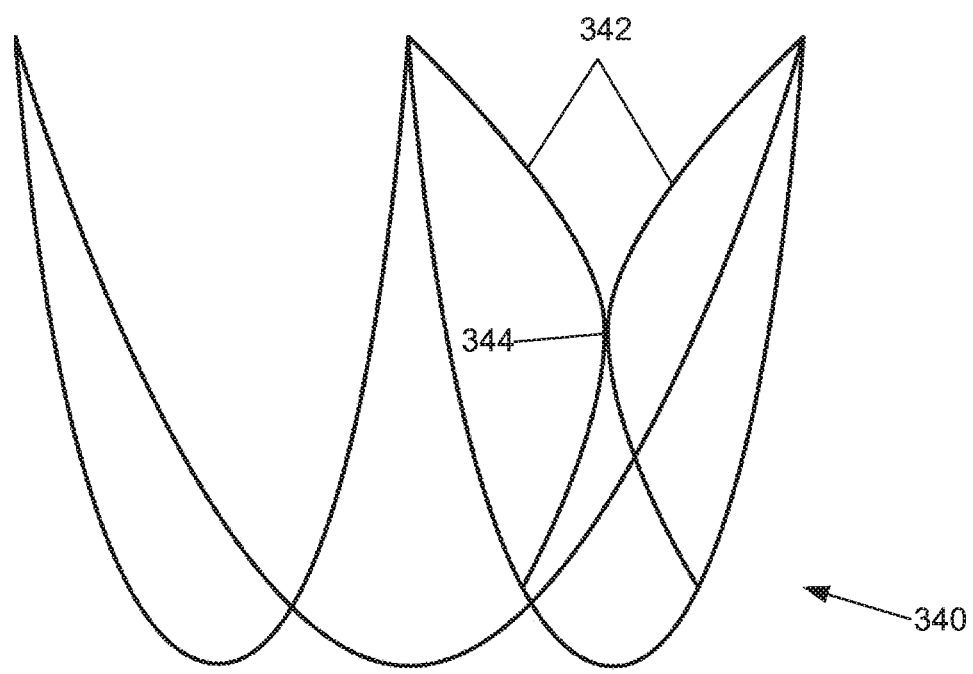
FIG. 18 is a diagrammatic illustration of a stent having reinforcing members in accordance with a third embodiment of the invention, with the reinforcing members acting as locking formations.

In still a further embodiment, a stent (340) shown in FIG. 18 has reinforcing members (342) that overlap each other when the stent (340) is in a compressed condition and abut in the expanded condition.

Each reinforcing member (342) is a bowed element, and preferably laterally flexible, extending between the end of a haunch and the arc and being directed in the direction of the opposite haunch and arranged such that the apexes (344) of adjacent bowed elements (342) abut with each other in the expanded condition. In this way collapsing of the stent (340) from the expanded condition is prevented.

In addition to annular support, the stent must be sufficiently stable to ensure proper opening and closing of the leaflets. This may require that the stent includes additional reinforcing members that are attached at or near the peaks of the commissural posts.

FIGS. 19 and 20 are diagrammatic representations of the stent which includes different reinforcing members (350, 360) that are attached at or near the peaks of the commissural posts. The reinforcing members (350, 360) provide additional strength to the stent, while reducing stresses in the leaflets.

Figure 19A:
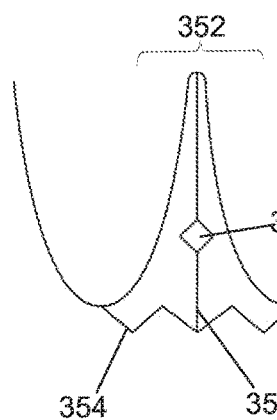
FIG. 19A is a diagrammatic illustration of a stent having reinforcing members that include a post with a diamond-shaped element.
Figure 19B:
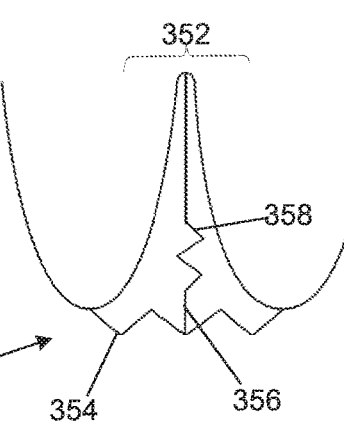
FIG. 19B is a diagrammatic illustration of a stent having reinforcing members that include a post with a concertina-shaped portion along its length.
Figure 19C:
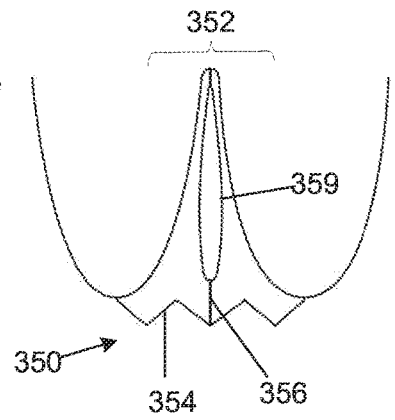
FIG. 19C is a diagrammatic illustration of a stent having reinforcing members that include a post with a looped element.

FIGS. 19A to 19C illustrate different embodiments of reinforcing members (350) that are positioned within the commissural posts (352) of the stent. The reinforcing members (350) provide additional support to the stent during opening and closing of the leaflets, and reduce twisting of the stent during deployment or valve operation in the body. The different embodiments in FIGS. 19A to 19C allow for the posts (352) to lengthen during compressing of the stent and shorten during expansion of the stent, to accommodate height changes in the arch-shaped elements.

A concertina-like strut (354) extends between adjacent arcs with a post (356) extending centrally from each strut (354) to the commissural post. In FIG. 19A the post (356) includes a diamond-shaped element (357) in its length which acts to enhance the structural support provided by the reinforcing member (350). As shown in FIG. 19B, the post (356) could also have a concertina-like portion (358) along its length or, as shown in FIG. 19C, a looped element (359). Alternatively, such posts may be positioned between the arch-shaped elements, extending from the arc to concertina-like struts between adjacent commissural posts.

Figure 20A:
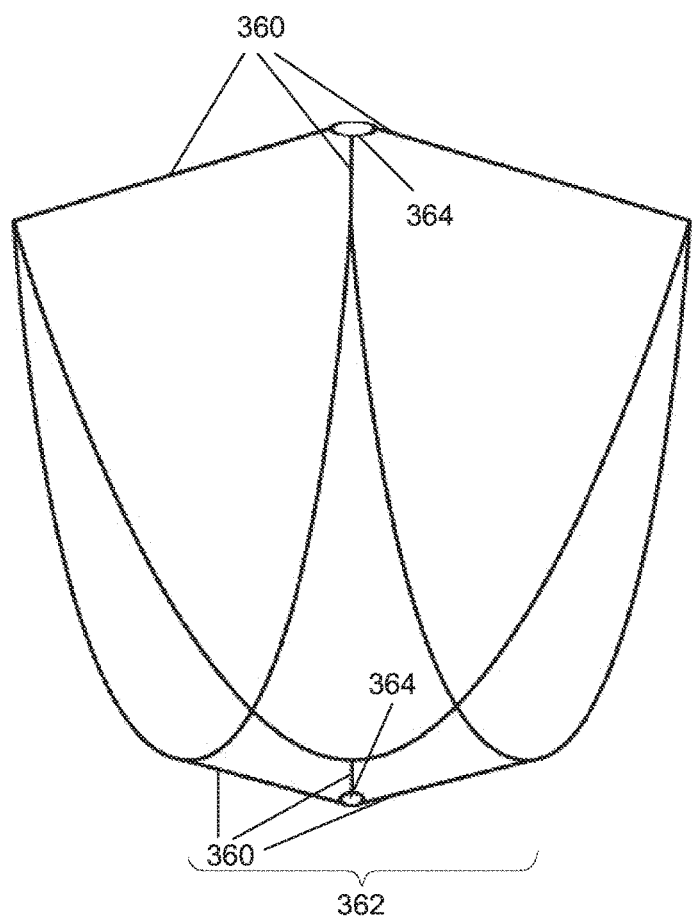
FIG. 20A is a diagrammatic illustration of a stent which includes reinforcing members at an inlet and an outlet end thereof.
Figure 20B:
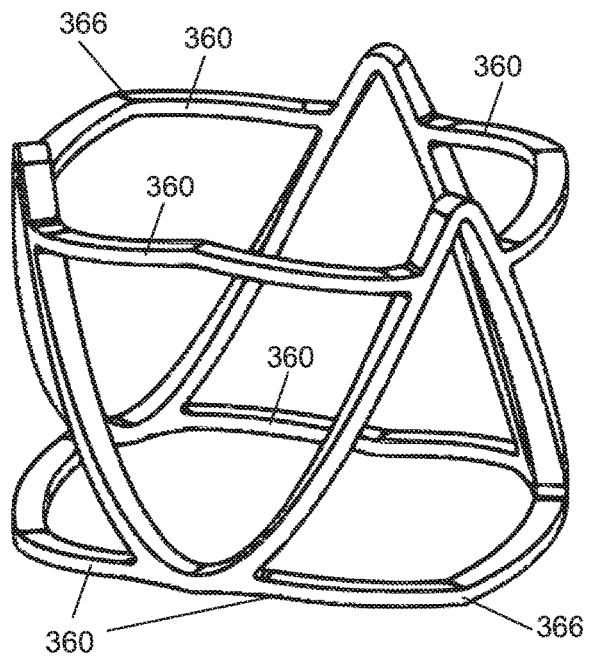
FIG. 20B illustrates a three-dimensional view of an embodiment of a stent in accordance with the invention, in which the stent includes reinforcing members at an inlet and an outlet end thereof.
Figure 20C:
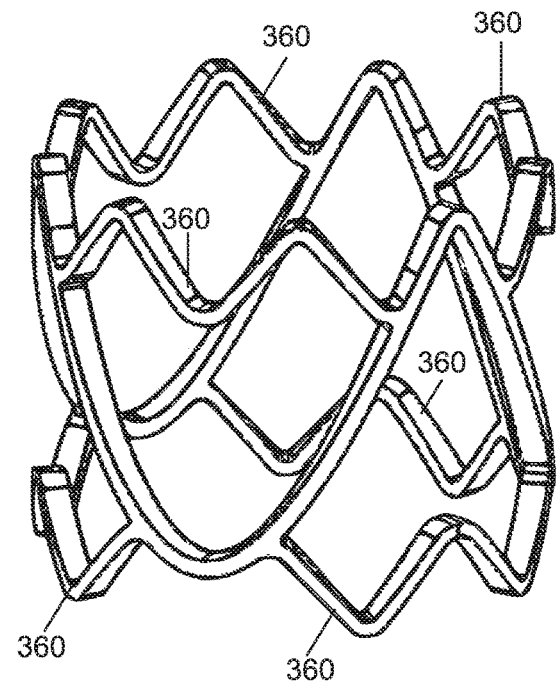
FIG. 20C illustrates a three-dimensional view of an embodiment of a stent in accordance with the invention, in which the stent includes reinforcing members at an inlet and an outlet end thereof.

FIGS. 20A to 20C illustrate three further embodiments of reinforcing members (360) that extend from a stent at the peaks of the commissural posts (362). The reinforcing members (360) on the inlet end are located between the arc of adjacent arch-shaped elements beneath the commissural posts (362), and provide securement of the valve within the annulus. Furthermore, the reinforcing members (360) ensure the stability of the arch-shape and ensure the correct shape of the leaflet is attained after compressing and expansion of the valve. The reinforcing members (360) on the outlet end are located between adjacent commissural posts (362) and provide structural support to the stent to prevent prolapse of the valve due to the leaflet free edge pulling the commissural posts to the centre of the valve during valve closure.

The reinforcement at the outlet end (the commissural post end) and inlet end (the arc end) of the stent satisfy different but complimentary purposes. The reinforcements at the outlet end provide structural support and prevent prolapse of the valve due to the leaflet free edge pulling the posts towards the central axis. The inlet end reinforcements primarily provide securement of the valve within the annulus and may be used to ensure stability of the arc portion of the arch-shaped elements and to ensure that the correct shape of the leaflet is attained after compressing and expansion of the valve.

In the embodiment shown in FIG. 20A, the reinforcing members (360) extend radially inward from each commissural post (362) to join at a central hub (364). The hub (364) is a circular element in the embodiment illustrated in FIG. 20A, but it could have any suitable configuration. As the stent is expanded, the reinforcing members (360) slide towards the arch-shaped members, with the hub moving toward the stent, thereby providing extensive support.

The embodiment shown in FIG. 20B is an embodiment of the principle illustrated in FIG. 14. In this embodiment, reinforcing members (360) extend between the arcs and the peaks of the commissural posts of adjacent arch-shaped elements, each having a central kink (366) about which the elements bend when in the compressed condition. Alternatively, as shown in FIG. 20C, the reinforcing members (360) can be concertina-shaped.

Figure 21:
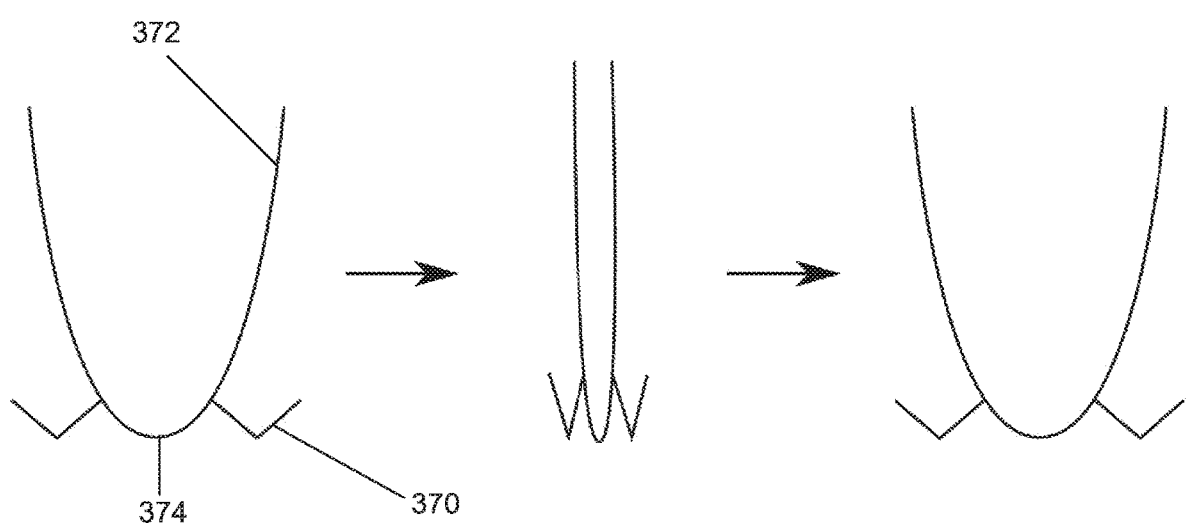
FIG. 21 is a diagrammatic illustration of how reinforcing members serve to maintain the shape of an arch-shaped element upon compression and expansion of the stent.

FIG. 21 is a diagrammatical illustration of how reinforcing members (370) serve to maintain the arch-shape of the arch-shape elements (372). As shown, the stent may have reinforcing members (370) similar to the reinforcing members shown in FIG. 20C that span between the arcs (374) of adjacent arch-shaped elements (372). These reinforcing members (370) support the stent by ensuring that the arch-shape of the arch-shape elements (372) is maintained after compressing and expanding of the stent, and thereby ensure proper functioning of the leaflets.

Figure 22:
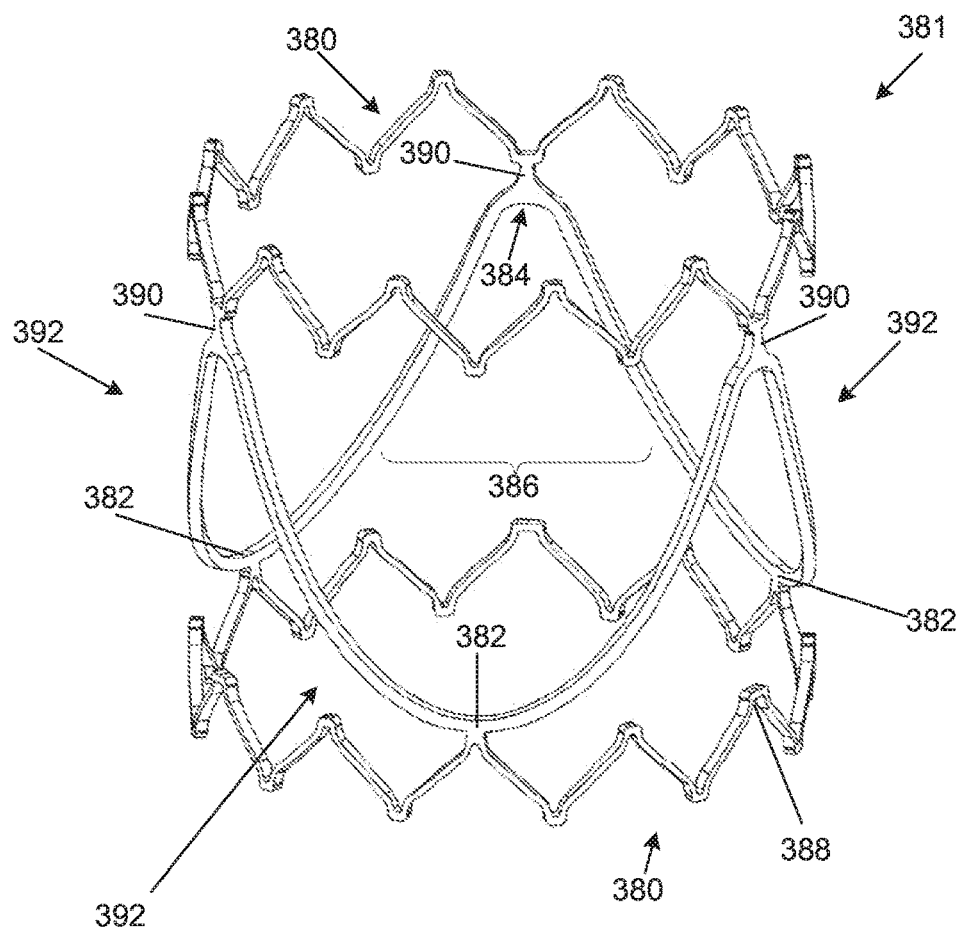
FIG. 22 illustrates a three-dimensional view of an embodiment of a stent in accordance with the invention which includes reinforcing members.

In FIG. 22, reinforcing members (380) are attached to the apex of the arcs (382) and peaks (384) of the commissural posts (386) of a stent (381).

As shown in FIG. 22, bends (388) in the concertina-shaped reinforcing members (380) may be hairpin-shaped to permit plastic deformation at each bend (388). Also, the points of attachment of the elements (380) to the commissural posts (386) are thickened by the inclusion of a short post (390) which more evenly distributes stress in the commissure posts due to bending.

In FIG. 22, the arch-shaped elements (392) include a radius at the peaks (384) of the commissural posts (386). Such a design for the arch-shaped elements (392) may still allow the leaflet to be continuously attached along the length of the arch-shaped elements (392) despite the leaflets having attachment edges that form peaks at the commissural posts without incorporating the said radius.

It should be appreciated that in stents which are expandable using an inflatable balloon or similar device, the hairpin bends undergo plastic deformation, while in self-expanding stents they remain elastic throughout compression and expansion. Thus, were the stent in FIG. 22 intended to be self-expanding, then the reinforcing elements would be shaped to permit full elastic expansion.

As is described above, it is envisioned that the width of the arch-shaped elements may also be varied along their lengths to reduce or evenly distribute stresses formed due to compressing and expanding of the stent. This is illustrated in FIGS. 23 to 24.

Figure 23:
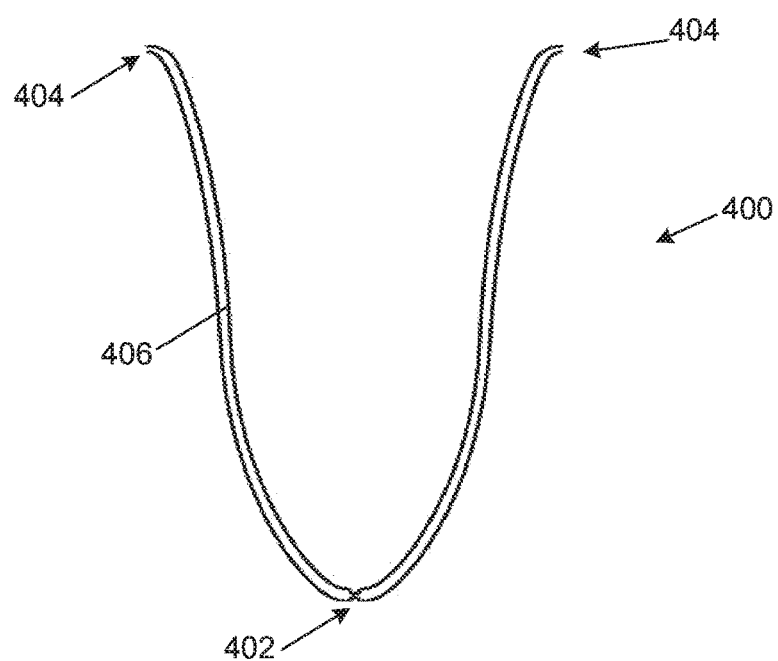
FIG. 23 is a diagrammatic illustration of an arch-shaped element in which the arc and peaks of the haunches are of a reduced width.

As shown in FIG. 23, an arch-shaped element (400) has an arc (402) and peaks (404) at the ends of the haunches (406) of reduced width. These are the areas of greatest curvature during compressing and expanding of the stent and will therefore typically be subject to high stresses, which may cause the arch-shaped elements (400) to undergo plastic deformation in these areas. Excessive plastic deformation may result in the stent being incapable of being expanded to its intended expanded condition and may cause the development of additional stresses within the leaflets, thus reducing longevity of the leaflets or reducing the effectiveness of the prosthetic heart valve. Reducing the width of the arch-shaped elements (400) in these areas reduces the local stresses formed in the arc (402).

Alternatively, strain can be substantially evenly distributed in the arch-shaped element. As shown in FIG. 24, an arch-shaped element (410) can have its arc (412) and peaks (414) at the ends of the haunches (416) wider than the remainder of the arch-shaped element (410). This reduces peak strains in the material and thereby also reduces peak strains and stresses in the leaflets at their attachment sites.

Figure 24:
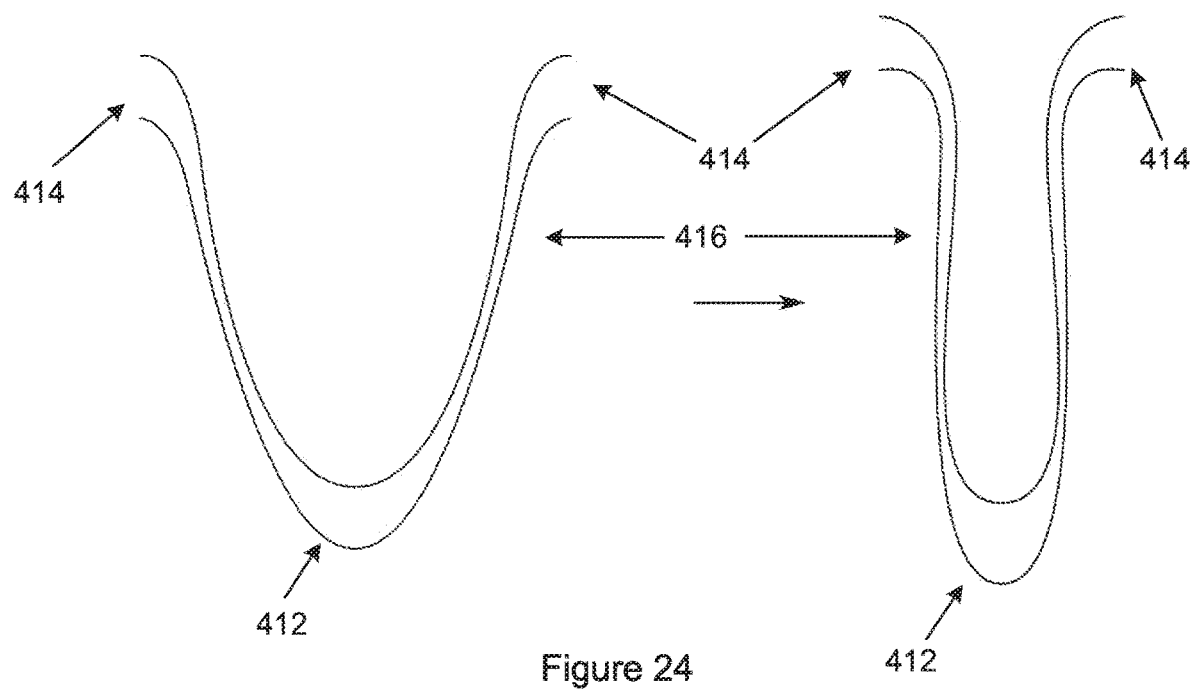
FIG. 24 is a diagrammatic illustration of an arch-shaped element in which the arc and peaks of the haunches are of an increased width.
Figure 25:
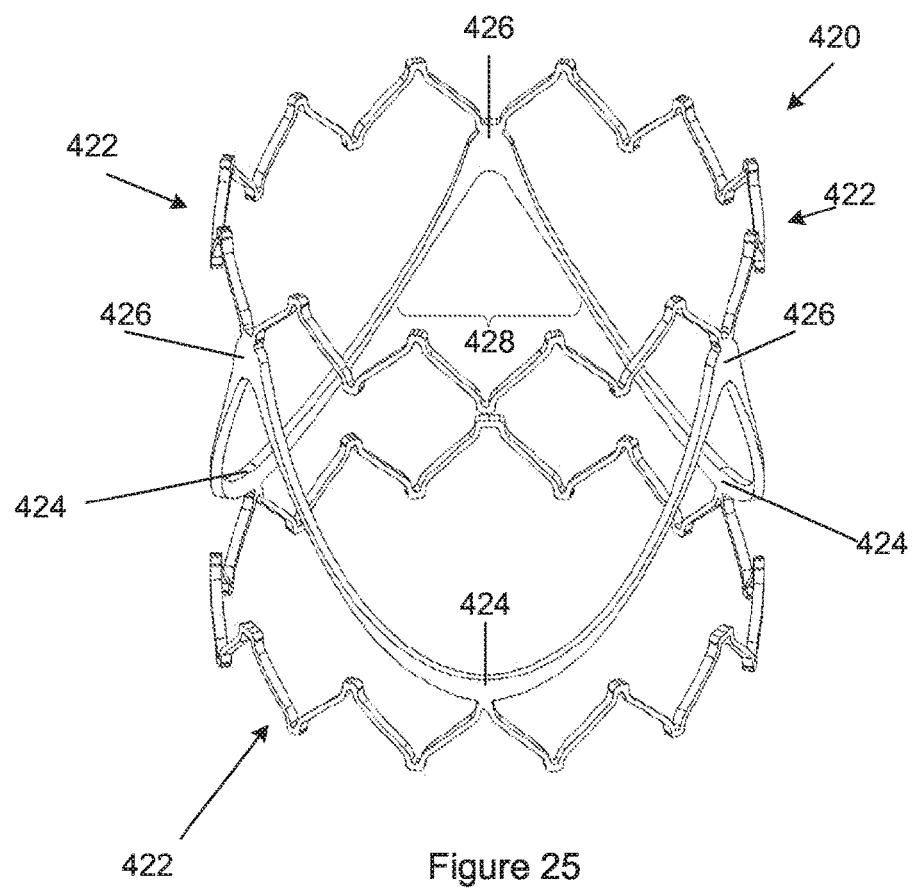
FIG. 25 illustrates a three-dimensional view of an embodiment of a stent in accordance with the invention which includes reinforcing members and in which the arch-shaped elements have varying widths.

The embodiment shown in FIG. 25 combines the embodiment shown in FIG. 22 with the structural adaptation illustrated in FIG. 24. The stent (420) in FIG. 25 therefore includes reinforcing members (422) having hairpin-shaped bends attached to arcs (424) and peaks (426) of the commissural posts (428) of increased width.

Alternatively, the stent may be reinforced by means of elongate posts attached to the arcs and peaks of commissural posts or to other reinforcing members, such as the ones described above.

Figure 26:
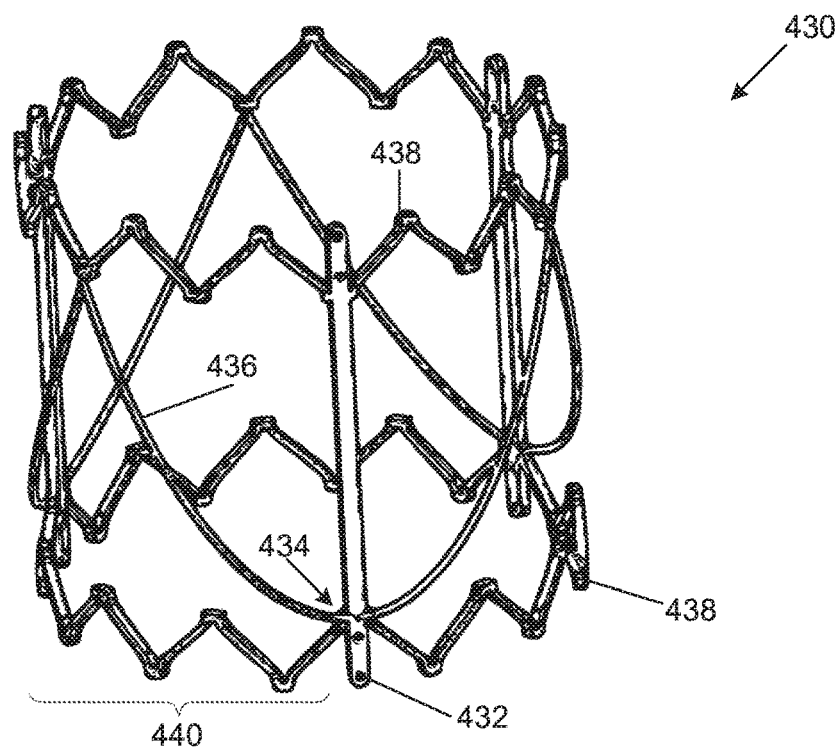
FIG. 26 illustrates a three-dimensional view of an embodiment of a stent in accordance with the invention which includes reinforcing members and additional elongate posts attached to the arcs of the arch-shaped elements.

FIGS. 26 to 31 illustrate embodiments of stents according to the invention, wherein elongate reinforcing posts are provided for structural support. In FIG. 26, the stent (430) is similar to the stent illustrated in FIG. 20C except that, in this embodiment, the stent (430) further includes elongate posts (432) which are attached to the arcs (434) of the arch-shaped elements (436) and the concertina-shaped reinforcing members (438). The structural posts (432) extend generally along the axes of the commissural posts (440). The elongate posts (432) in combination with the reinforcing members (438) serve to provide structural support and stent (430) stability. The commissural posts (440) are flexible and free to move inwardly during closing of the leaflets.

Figure 27:
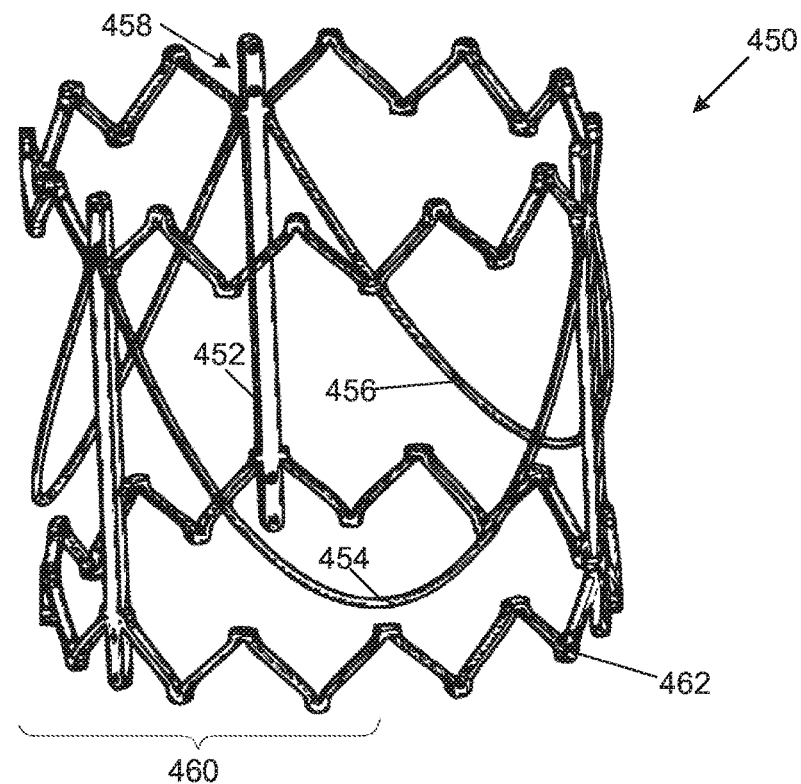
FIG. 27 illustrates a three-dimensional view of an embodiment of a stent in accordance with the invention which includes reinforcing members and additional elongate posts attached to the commissural posts.

The stent (450) illustrated in FIG. 27 is similar to the stent (430) illustrated in FIG. 26 except that, in this embodiment, the posts (452) are not attached to the arcs (454) of the arch-shaped elements (456), but rather to the peaks (458) of the commissural posts (460). The posts (452) thus have a similar function to the reinforcing members (357, 358, 359) illustrated in FIGS. 19A to 19C. Furthermore, the reinforcing members (462) of this embodiment are attached to the posts (452) and not the arcs (454) of the arch-shaped elements (456). This serves to facilitate compressing and expansion of the stent, and permits for the reinforcing members at the inlet end to be inflated to a different final diameter than the arch-shaped elements (456) if desired. This may be desirable to reduce leakage and to improve securement of the stent (430) in the annulus, while at the same time retaining the valve diameter at its desired dimension for proper functioning of the valve.

Figure 28:
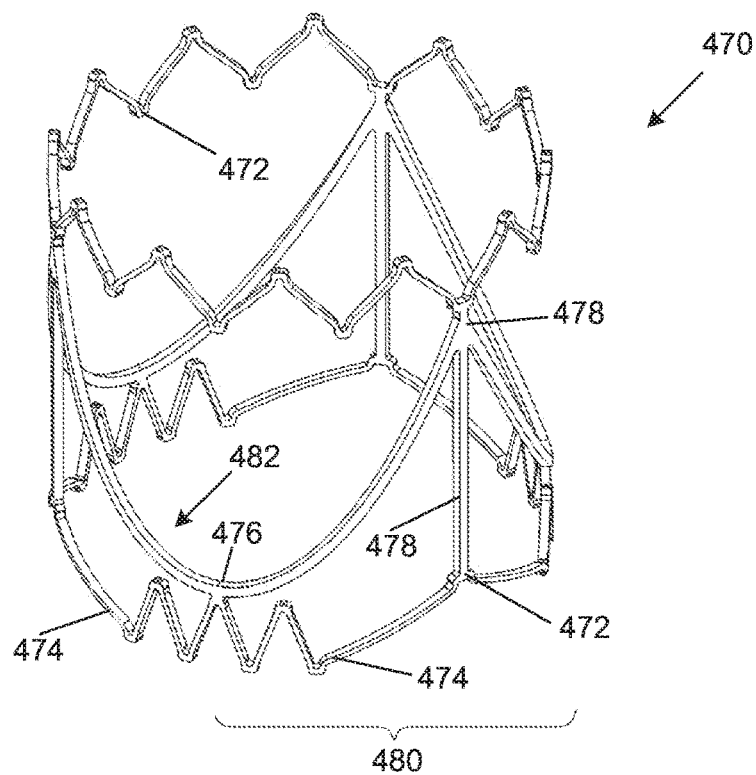
FIG. 28 illustrates a three-dimensional view of an embodiment of a stent in accordance with the invention which includes reinforcing members and additional elongate posts attached to the commissural posts.

FIG. 28 illustrates a stent (470) which includes reinforcing members (472) comprising struts (474) extending between adjacent arcs (476) with posts (478) extending centrally from each strut (474) to the peaks (478) of the commissural posts (480) as illustrated in FIGS. 19A to 19C in addition to reinforcing members such as those illustrated in FIG. 20C. The reinforcing members (472) in this embodiment are attached to the arcs (476) as well as the peaks (478) of the commissural posts (480) of the arch-shaped elements (482). The addition of the reinforcing members (472) will permit the stent (470) to lengthen during compression and shortening during expansion, while retaining its overall structural integrity for proper operation of the valve once the stent (470) has been expanded.

Figure 29:
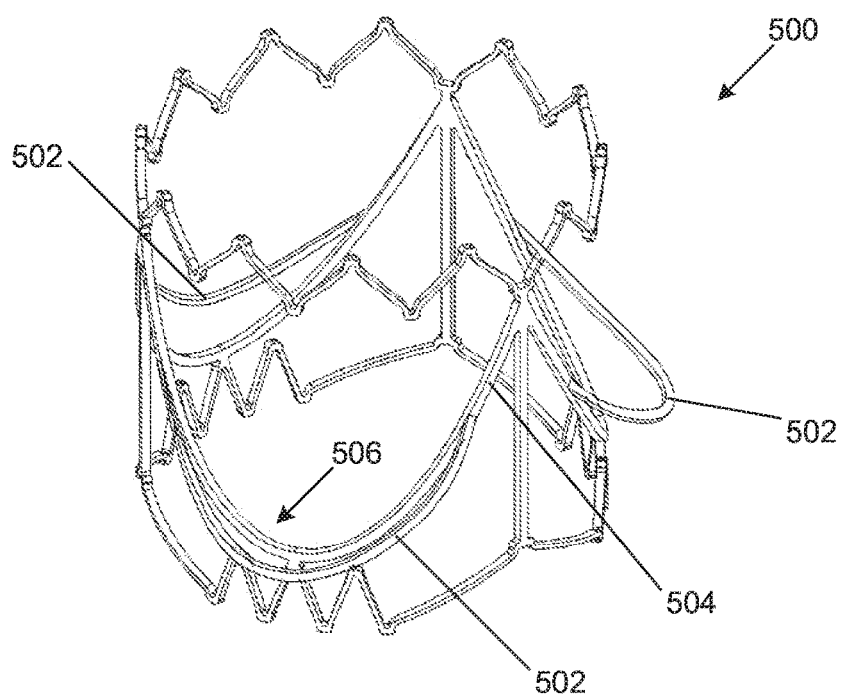
FIG. 29 illustrates a three-dimensional view of an embodiment of a stent similar to that of FIG. 28, wherein the stent further includes locating members.

In FIG. 29, the stent (500) further includes three locating members (502) that extend outwardly from the body of the stent (500) and that assist in correctly locating the stent (500) within the cusps of the natural heart valve during deployment of the valve. In this embodiment, the locating members (502) are loops attached to the stent (500) or integrally formed with the stent (500), such as during laser cutting, at corresponding points on the haunches (504) of each arch-shaped element (506). The locating members (502) are configured to be deployed into a position wherein the loops extend beyond the expanded condition of the stent (500). This allows the (500) stent to be located within the cusps of the natural heart valve, thereby ensuring that the valve is expanded and deployed in a desired location relative to the natural heart valve.

Figure 30:
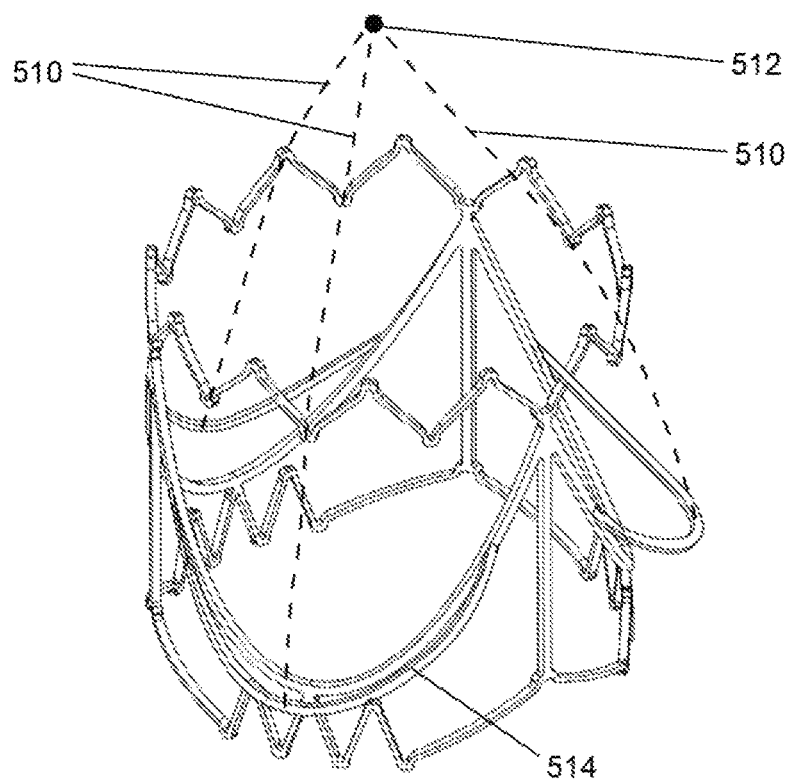
FIG. 30 is an illustration of how the locating members of FIG. 29 may be deployed by means of tethers attached to a deployment device.

It is foreseen that locating members on a stent may be deployed into a position wherein the locating members extend beyond the expanded condition of the stent by means of, for example, tethers or "strings" forming part of a valve deployment device which pull the locating members from a position wherein they abut the haunches to the deployed position. The broken lines (510) in FIG. 30 illustrates an example of how strings can be attached to a deployment device at a point (512) on the deployment device (not shown) and to the locating members (514), as are illustrated in FIG. 29. In the case of a self-expanding stent, the locating members may be manufactured from an appropriate shape-memory material so as to automatically move into a desired deployed condition when the stent is expanded. Alternatively the locating members may be made from a superelastic or self-expanding material even where the reinforcing members of the stent are balloon-expandable. Further methods of deploying the locating members are to allow them to be unrestrained at their apices and therefore preferentially inflated by a balloon to expand beyond the diameter of the ring-like body of the stent. Yet a further method of deploying the location arms is to provide linkage members that force the arms to extend outwards during expansion of the stent.

Figure 31:
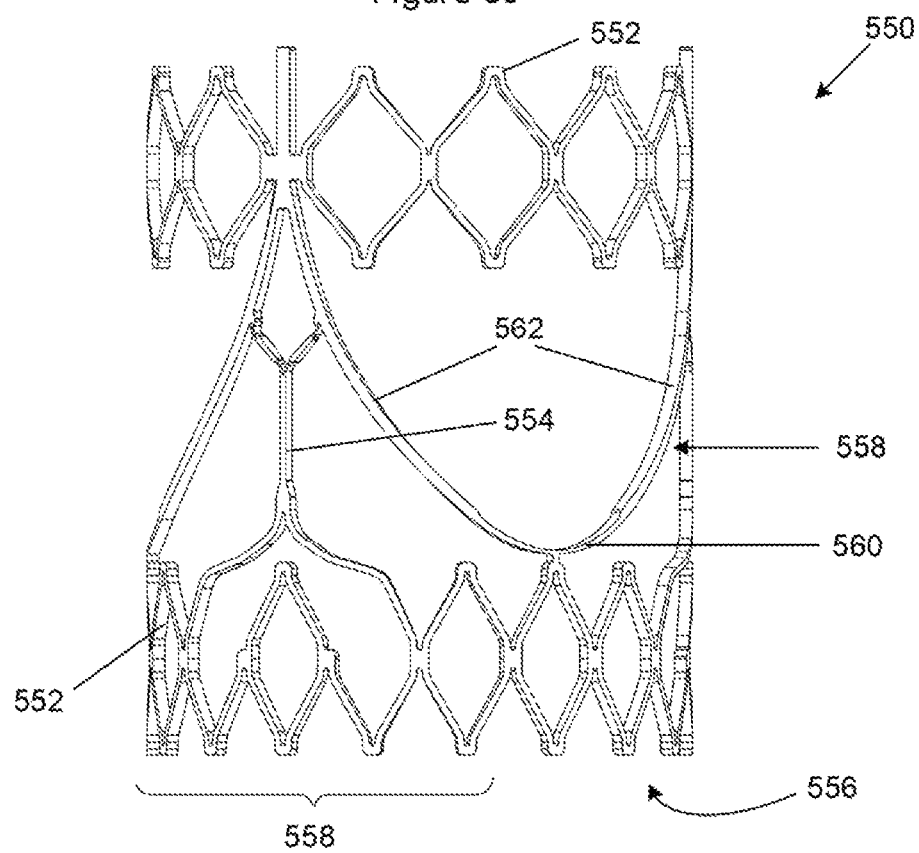
FIG. 31 illustrates a front view of an embodiment of a stent in accordance with the invention which includes reinforcing members at the inlet and outlet ends of the valve, with additional elongate post attached to the commissural posts.

FIG. 31 illustrates a further embodiment of a stent (550) in accordance with the invention, in which the reinforcing members (552) of the stent (550) are diamond shaped. It has been found that having diamond shaped reinforcing members (552) may significantly increase the stability of such members, particularly during compressing and expanding of the stent (550). Further, the stent (550) includes longitudinal posts (554) that are attached to the reinforcing members (552) at the inlet end (556) of the stent (550) and the commissural posts (558). The longitudinal posts (554) are able to lengthen and shorten during compressing and expanding of the stent (550), while at the same time providing the stent (550) with increased longitudinal strength. In addition, the arch-shaped elements (558) of the stent (550) vary in thickness along their length, in this embodiment the arcs (560) being thinner than the haunches (562).

The stent may further include biasing members that are capable of at least partial elastic deformation during compression of the stent and which act on adjacent haunches to bias the haunches from the compressed condition to the operative condition. Alternatively, the stent may further include biasing members that are capable of undergoing at least partial plastic deformation during compression and expansion of the stent.

The biasing members may extend between the haunches of each arch-shaped elements, or they may extend between the haunches of adjacent arch-shaped elements, thus in the commissural posts. Alternatively, the biasing members may extend around the peaks of the commissural posts.

Figure 32:
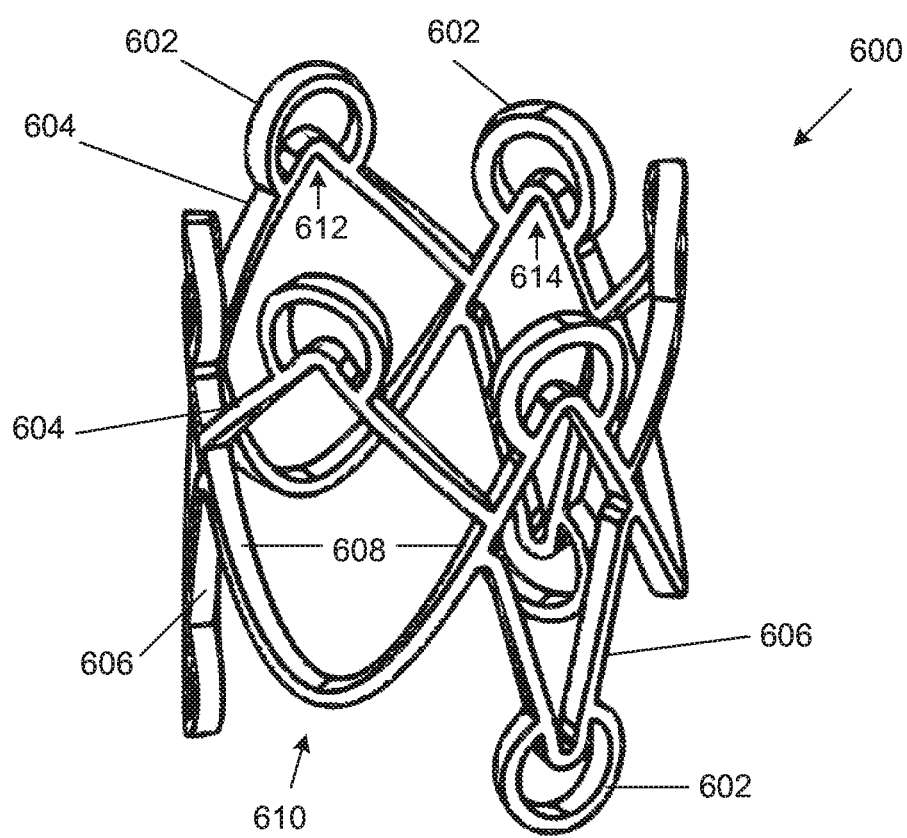
FIG. 32 illustrates a three-dimensional view of an embodiment of a stent in accordance with the invention in which the stent includes both elastically deformable and plastically deformable structural members.

An example of such a stent is illustrated in FIG. 32, wherein the stent (600) includes elastically deformable, C-shaped elements (602) and plastically deformable, V-shaped struts (604, 606). In the embodiment illustrated, three struts (604) extend between inner edges of the haunches (608) of each arch-shaped element (610), and three struts (606) extend between outer edges of the haunches (608) of adjacent arch-shaped elements (610). The ends of the C-shaped elements (602) extend from the outer surface of the arms of the struts (604, 606) respectively on opposite sides of the apex (612), and from the outer surface of the haunches on opposite sides of the commissural peaks (614).

The V-shaped struts (604, 606) open in a predominantly plastic manner during stent expansion, but some elastic recoil occurs when the expansion mechanisms are removed. The C-shaped elements (602) however bias the struts (604, 606) apart. This encourages the stent (600) into an open condition and assists in maintaining the stent (600) in this condition. The C-shaped elements (602) at the commissural peaks (614) similarly bias the arch-shaped elements (610) into a further open or operative condition. The combination of plastic and elastic members prevents recoil of the stent (600) during expansion thereof.

In a preferred embodiment of the invention, the stent is balloon expandable, however, the stent may also be self-expanding or both balloon expandable and self-expandable. Thus, for example, it may have features that permit partial self-expanding, whereafter full deployment is achieved through expansion by a balloon. In such an embodiment, the arch-shaped elements may be made from a shape-memory material such as Nitinol and the reinforcing members as well as other structural members may be made from an alloy such as cobalt chromium. The combination of different materials will have the effect that the arch-shaped elements will self-expand during deployment, whereas the other structural members will require balloon expansion.

The combination of balloon expandable and self-expandable features may also be achieved by using a single material and then heat-treating the arch-shaped elements or reinforcing members, thereby changing their material properties. For example, the stent may be made from a full-hard material, with the reinforcing members heat-treated so as to provide far greater elongation during plastic deformation thereof and hence cause work-hardening during deployment. Similarly, any locating members may be constructed from full-hard material.

The above description is by way of example only and it will be understood that numerous variations may be made to the implementation of the invention that is described above without departing from the scope hereof.

The invention claimed is:

1. A prosthetic heart valve which includes a stent having three leaflets attached thereto, the stent being compressible to a compressed condition in which it is capable of being introduced into a patient's body through a minimally invasive procedure and further being expandable from the compressed condition to an operative condition during deployment of the valve within the patient's body, the stent having a ring-like body with an inlet and an outlet and defining in its height three arch-shaped elements each of which has an arc and a pair of haunches extending from opposite sides thereof, with three commissural posts formed by the haunches of adjacent arch-shaped elements, wherein primary reinforcing members are provided that span between adjacent commissural posts of the arch-shaped elements and which act to strengthen the stent so as to support the leaflets during operation of the valve, and wherein secondary reinforcing members extend between the haunches of adjacent arch-shaped elements, wherein the secondary reinforcing members are spaced apart along the length of the haunches, and additional reinforcing members provided below the arcs of the arch-shaped elements which assist in securing the stent within the valve annulus and further assist in maintaining the arch-shape of the arch-shaped elements during compression and expansion of the valve so as to ensure that the valve is able to return to its operative condition after compression thereof, and wherein the width of the arch-shaped elements varies along their length with the arcs and peaks at the ends of the haunches being wider than the remainder of the arch-shaped elements, the variation in width ensuring that stresses in the arch-shaped elements are kept at a minimum during expansion and compression of the stent while ensuring that the stent is capable of returning to its operative condition after compression and expansion thereof, each leaflet having an attachment edge and a free edge with a belly extending between the free edge and the attachment edge, the leaflets being movable between an open condition, in which fluid flow through the valve is permitted in a direction from the inlet to the outlet, and a coapted condition, in which the free edges abut and prevent fluid flow through the valve in an opposite direction from the outlet to the inlet, wherein the leaflets are made from a polymeric material and are attached to the stent by moulding to thereby encapsulate the arch-shaped elements so that the attachment edge of each leaflet is continuously attached along the length of an arch-shaped element, and wherein the arch-shape is defined by a parametric curve and its mirror image along the z-axis which is wrapped about a cylinder having a diameter of the prosthetic heart valve, with the parametric curve being defined by a function $A(x)=(1-x)^3 P_0 + 3(1-x)^2 x P_1 + 3(1-x) x^2 P_2 + x^3 P_3$, with $P_0$ to $P_3$ being control points, wherein $P_0$ and $P_3$ are selected on the basis of the diameter and height of prosthetic heart valve, and wherein $P_1$ is selected from the range of $0 \leq z \leq H$ and $P_2$ is selected from the range $0 \leq x \leq \pi D/6$ where H is the height and D the diameter of the prosthetic heart valve.

2. A prosthetic heart valve as claimed in claim 1, wherein the shape of the free edge of the leaflets is defined by three curves defined by functions $y=mx$ with $-c_b \leq x < -c_b + x_s$, $y=K \cos(Lx)+t$ with $-c_b + x_s \leq x < c_b - x_s$, and $y=-mx$ with $c_b - x_s \leq x \leq c_b$ with $c_b$ being defined as the end points of the free edge, $x_s$ being a function of the straight line portion of the free edge where the free edge is secured to the commissural posts, the constant m being in the range of 0.1 to 1, the constant K being in the range of −3 to 0, the constant L being in the range of 0.05 to 1.5, and the constant t being in chosen such that the end points of the three curves meet each other.

3. A prosthetic heart valve as claimed in claim 1, wherein the belly is defined by a parametric curve in a two dimensional x-y plane, with the parametric curve being defined by a function $B(x)=(1-x)^3 P_0 + 3(1-x)^2 x P_1 + 3(1-x) x^2 P_2 + x^3 P_3$, with $P_0$ to $P_3$ being control points, wherein $P_2$ and $P_3$ remain constant, and wherein $P_0$ is selected from the range of $0.3D \leq P_{0x} \leq 0.5D$ and $0.5H \leq P_{0y} \leq 0.8H$ and $P_1$ is selected from the range $0.4D \leq P_{1x} \leq 0.6D$ and $0.3H \leq P_{1y} \leq 0.8H$ where H is the height and D the diameter of the prosthetic heart valve.

4. A prosthetic heart valve as claimed in claim 1, wherein one or more openings are provided between the haunches of adjacent arch-shaped elements.

5. A prosthetic heart valve as claimed in claim 1, wherein the stent includes biasing members capable of at least partial elastic deformation during compression of the valve and which act on adjacent haunches to bias the haunches from the compressed condition to the operative condition.

6. A prosthetic heart valve as claimed in claim 1, wherein the valve includes locating members which extend outwardly from the body of the stent to locate the valve within a natural heart valve of a patient during deployment thereof.

7. A prosthetic heart valve as claimed in claim 1, wherein the primary reinforcing members are configured to secure the stent within a valve annulus.

8. A prosthetic heart valve as claimed in claim 1, wherein the leaflets are manufactured from a polymeric material and attached to the stent by a spray moulding process comprising:

pre-moulding the leaflets to an intermediate thickness by spray coating a mould;

pre-coating the stent with the same or a similar polymeric material used for the leaflets by spray coating the stent; and placing the pre-coated stent onto the mould and providing a final spray coat to the leaflets and the stent so as to increase the leaflet thickness to a desired final thickness and encapsulate the complementary shaped arch-shaped element of the stent to thereby ensure that the attachment edge of each leaflet is continuously attached along the length of the complementary shaped attachment surface of the stent.

9. A prosthetic heart valve as claimed in claim 8, wherein the mould is rotated during drying of the polymeric material so as to ensure that no droplets are formed.

10. A stent for a prosthetic heart valve, the stent configured to house three polymeric leaflets and being compressible to a compressed condition, in which it is capable of being introduced into a patient's body through a minimally invasive procedure and further being expandable from the compressed condition to an operative condition during deployment of the valve within the patient's body, the stent having a ring-like body with an inlet and an outlet and defining in its height three arch-shaped elements each of which having an arc and a pair of haunches extending from opposite sides thereof, with three commissural posts formed by the haunches of adjacent arch-shaped elements, wherein primary reinforcing members are provided that span between adjacent commissural posts of the arch-shaped elements and which act to strengthen the stent so as to support the leaflets during operation of the valve, and wherein secondary reinforcing members extend between the haunches of adjacent arch-shaped elements, wherein the secondary reinforcing members are spaced apart along the length of the haunches, and additional reinforcing members provided below the arcs of the arch-shaped elements which assist in securing the stent within the valve annulus and further to assist in maintaining the arch-shape of the arch-shaped elements during compression and expansion of the valve so as to ensure that the valve is able to return to its operative condition after compression thereof, and wherein the width of the arch-shaped elements varies along their length with the arcs and peaks at the ends of the haunches being wider than the remainder of the arch-shaped elements, the variation in width ensuring that stresses in the arch-shaped elements are kept at a minimum during expansion and compression of the stent while ensuring that the stent is capable of returning to its operative condition after compression and expansion thereof, wherein each arch-shaped element provides an attachment zone along which an attachment edge of a leaflet can be continuously attached to the stent, and wherein the arch-shape is defined by a parametric curve and its mirror image along the z-axis which is wrapped about a cylinder having a diameter of the prosthetic heart valve, with the parametric curve being defined by a function $A(x)=(1-x)^3 P_0 + 3(1-x)^2 x P_1 + 3(1-x)x^2 P_2 + x^3 P_3$, with $P_0$ to $P_3$ being control points, wherein $P_0$ and $P_3$ are selected on the basis of the diameter and height of prosthetic heart valve, and wherein $P_1$ is selected from the range of $0 \leq z \leq H$ and $P_2$ is selected from the range $0 \leq x \leq \pi D/6$ where H is the height and D the diameter of the prosthetic heart valve.

11. A stent as claimed in claim 10, wherein the stent includes biasing members capable of at least partial elastic deformation during compression of the stent and which act on adjacent haunches to bias the haunches from the compressed condition to the operative condition.

12. A stent as claimed in claim 10, wherein the stent includes locating members which extend outwardly from the body of the stent to locate the stent within a natural heart valve of a patient during deployment thereof.

13. A stent for a prosthetic heart valve as claimed in claim 10, wherein one or more openings are provided between the haunches of adjacent arch-shaped elements.

14. A stent as claimed in claim 10, wherein the primary reinforcing members are configured to secure the stent within a valve annulus.

* * * * *